United States Patent
Buchbinder et al.

(10) Patent No.: US 9,301,836 B2
(45) Date of Patent: Apr. 5, 2016

(54) CARDIAC VALVE SUPPORT STRUCTURE

(75) Inventors: Maurice Buchbinder, San Diego, CA (US); Julie A. Logan, La Jolla, CA (US)

(73) Assignee: MVALVE TECHNOLOGIES LTD., Herzliya (IL)

( * ) Notice: Subject to any disclaimer, the term of this patent is extended or adjusted under 35 U.S.C. 154(b) by 215 days.

(21) Appl. No.: 13/224,124

(22) Filed: Sep. 1, 2011

(65) Prior Publication Data

US 2012/0059458 A1 Mar. 8, 2012

Related U.S. Application Data

(60) Provisional application No. 61/379,235, filed on Sep. 1, 2010.

(51) Int. Cl.
*A61F 2/24* (2006.01)

(52) U.S. Cl.
CPC .............. *A61F 2/2418* (2013.01); *A61F 2/2409* (2013.01); *A61F 2/24* (2013.01); *A61F 2/2412* (2013.01); *A61F 2/2415* (2013.01); *A61F 2/2433* (2013.01); *A61F 2/2436* (2013.01); *A61F 2/2442* (2013.01); *A61F 2/2445* (2013.01); *A61F 2/2466* (2013.01); *A61F 2210/0014* (2013.01); *A61F 2220/0025* (2013.01); *A61F 2230/001* (2013.01); *A61F 2230/0006* (2013.01); *A61F 2230/0069* (2013.01); *A61F 2250/006* (2013.01); *A61F 2250/0036* (2013.01); *A61F 2250/0039* (2013.01); *A61F 2250/0069* (2013.01); *A61F 2250/0098* (2013.01)

(58) Field of Classification Search
CPC ................................... A61F 2/2409
See application file for complete search history.

(56) References Cited

U.S. PATENT DOCUMENTS

| | | | |
|---|---|---|---|
| 7,585,321 B2 | 9/2009 | Cribier | |
| 7,753,923 B2 | 7/2010 | St. Goar et al. | |
| 2002/0151970 A1 | 10/2002 | Garrison et al. | |
| 2004/0210306 A1 | 10/2004 | Quijano et al. | |
| 2005/0075713 A1 | 4/2005 | Biancucci et al. | |
| 2005/0075728 A1 | 4/2005 | Nguyen et al. | |
| 2005/0137689 A1 | 6/2005 | Salahieh et al. | |
| 2006/0235509 A1 | 10/2006 | Lafontaine | |
| 2007/0162103 A1 | 7/2007 | Case et al. | |
| 2008/0065204 A1* | 3/2008 | Macoviak et al. | 623/2.17 |
| 2008/0140189 A1 | 6/2008 | Nguyen et al. | |
| 2008/0249619 A1 | 10/2008 | Stacchino et al. | |
| 2009/0005863 A1 | 1/2009 | Goetz et al. | |
| 2009/0171432 A1 | 7/2009 | Von Segesser et al. | |
| 2009/0177277 A1 | 7/2009 | Milo | |
| 2010/0145440 A1* | 6/2010 | Keranen | 623/2.37 |

(Continued)

FOREIGN PATENT DOCUMENTS

| | | |
|---|---|---|
| CN | 1610529 A | 4/2005 |
| CN | 101374478 | 2/2009 |

(Continued)

OTHER PUBLICATIONS

Office Action dated Dec. 23, 2014 in Chinese App. No. 201180052374.2 (w/ partial English translation).
International Search Report issued in International Application No. PCT/US2011/050232 dated Apr. 12, 2012.
Written Opinion of the International Searching Authority issued in International Application No. PCT/US2011/050232 dated Apr. 12, 2012.

(Continued)

*Primary Examiner* — Yashita Sharma
*Assistant Examiner* — Rebecca Preston
(74) *Attorney, Agent, or Firm* — Nixon & Vanderhye P.C.

(57) ABSTRACT

Cardiac valve supports and their methods of use.

17 Claims, 20 Drawing Sheets

(56) References Cited

U.S. PATENT DOCUMENTS

| | | |
|---|---|---|
| 2010/0161036 A1 | 6/2010 | Pintor et al. |
| 2011/0137397 A1* | 6/2011 | Chau et al. .................. 623/1.11 |
| 2011/0319990 A1 | 12/2011 | Macoviak et al. |
| 2012/0016464 A1* | 1/2012 | Seguin .......................... 623/1.26 |
| 2012/0022629 A1 | 1/2012 | Perera et al. |

FOREIGN PATENT DOCUMENTS

| | | |
|---|---|---|
| CN | 101588771 A | 11/2009 |
| WO | WO 2007/089625 | 8/2007 |
| WO | WO 2008/070797 | 6/2008 |
| WO | WO 2012/031141 | 3/2012 |
| WO | WO 2012/174383 | 12/2012 |

OTHER PUBLICATIONS

International Preliminary Report on Patentability issued in International Application No. PCT/US2011/050232 dated Mar. 5, 2013.

International Search Report for PCT/IL2013/000025 mailed Jun. 18, 2013.

Written Opinion of the International Searching Authority for PCT/IL2013/000025 mailed Jun. 18, 2013.

Co-pending U.S. Appl. No. 14/471,575, filed Aug. 28, 2014 in the name of Buchbinder et al.

Extended European Search Report issued in Application No. 11822677.8 dated Aug. 17, 2015.

U.S. Office Action issued in U.S. Appl. No. 13/790,174 dated Jan. 25, 2016.

* cited by examiner

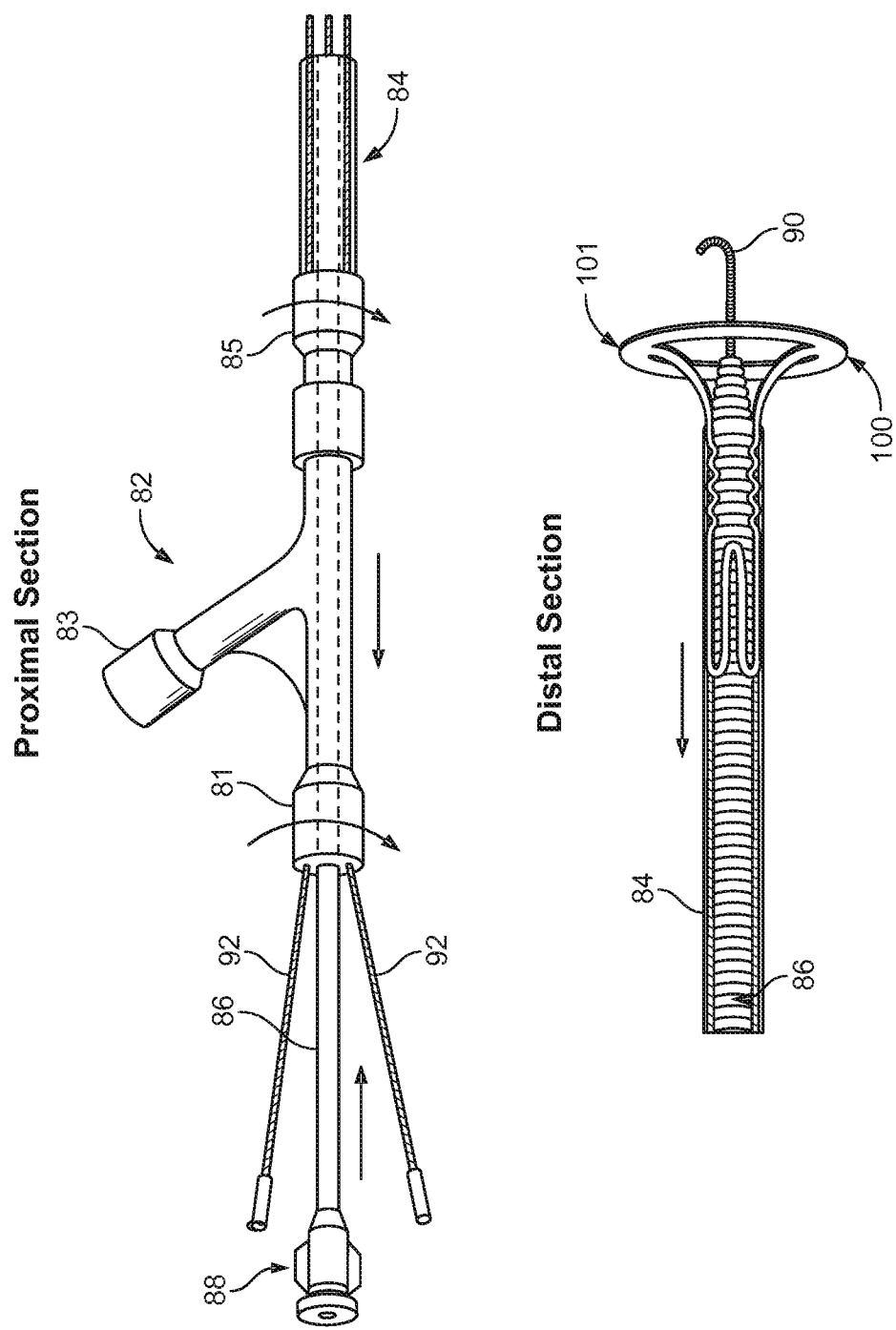

CARDIAC VALVE SUPPORT STRUCTURE

CROSS REFERENCE TO RELATED APPLICATIONS

This application claims the benefit of U.S. Provisional Application No. 61/379,235, filed Sep. 1, 2010, which is incorporated herein by reference in its entirety.

BACKGROUND OF THE DISCLOSURE

Heart valve regurgitation occurs when the heart leaflets do not completely close when the heart contracts. When the heart contracts, blood flows back through the improperly closed leaflets. For example, mitral valve regurgitation occurs when blood flows back through the mitral valve and into the left atrium when the ventricle contracts.

In some instances regurgitation occurs due to disease of the valve leaflets (e.g., primary, or "organic" regurgitation). Regurgitation can also be cause by dilatation of the left ventricle, which can lead to secondary dilatation of the mitral valve annulus. Dilation of the annulus spreads the mitral valve leaflets apart and creates poor tip cooptation and secondary leakage, or so-called "functional regurgitation."

Currently, primary regurgitation is corrected by attempting to remodel the native leaflets, such as with clips, sutures, hooks, etc., to allow them to close completely when the heart contracts. When the disease is too far advanced, the entire valve needs to be replaced with a prosthesis, either mechanical or biologic. Examples include suture annuloplasty rings all the way to actual valve replacement with leaflets, wherein the suture rings are sutured to the mitral valve annulus. Annuloplasty rings, which are also sutured to the annulus, have also been used to attempt to remodel the annulus, bringing the native leaflets closer together to allow them to properly close.

Based on the success of catheter-based aortic valve replacement there is growing interest in evaluating similar technologies to replace the mitral valve non-invasively using similar types of replacement valves.

Unlike the aortic valve, however, the mitral valve annulus does not provide a good landmark for positioning a replacement mitral valve. In patients needing a replacement aortic valve, the height and width of the aortic annulus are generally increased in the presence of degenerative disease associated with calcium formation. These changes in tissue make it easier to properly secure a replacement aortic valve in place due to the reduced cross-sectional area of the aortic annulus. The degenerative changes typically found in aortic valves are not, however, present in mitral valves experiencing regurgitation, and a mitral valve annulus is therefore generally thinner than the annulus of a diseased aortic valve. The thinner mitral valve annulus makes it relatively more difficult to properly seat a replacement mitral valve in the native mitral valve annulus. The general anatomy of the mitral valve annulus also makes it more difficult to properly anchor a replacement mitral valve in place. The mitral valve annulus provides for a smoother transition from the left atrium to the left ventricle than the transition that the aortic valve annulus provides from the aorta to the left ventricle. The aortic annulus is anatomically more pronounced, providing a larger "bump" to which a replacement aortic valve can more easily be secured in place.

In general, the aortic valve annulus is smaller than the mitral valve annulus. It has been estimated that the mitral valve annulus is about 2.4 cm to about 3.2 cm in diameter, while the aortic valve annulus has been estimated to be about 1.6 cm to about 2.5 cm in diameter.

The larger mitral valve annulus makes it difficult to securely implant current percutaneously delivered valves in the native mitral position. Current replacement aortic valves are limited in the amount of radial expansion they can undergo during deployment and implantation. To provide a replacement aortic valve that has an expanded configuration such that it can be securely anchored in a mitral valve annulus would require that the collapsed delivery profile of the replacement aortic valve be increased. Increasing the collapsed delivery profile, however, would make endovascular delivery more dangerous for the patient and more difficult to navigate the vasculature with a larger diameter delivery system.

Some attempts have been made to deliver and implant a one-piece replacement mitral valve, but it is difficult to provide a device that can be collapsed down to have a sufficiently small delivery profile and still be able to be expanded and secured in place within the mitral valve via a vascular access site.

A valve support structure or anchoring device is needed that can be positioned near or within the native mitral valve and that is adapted to secure a replacement mitral valve in place.

SUMMARY OF THE DISCLOSURE

One aspect of the disclosure is a cardiac valve support adapted for endovascular delivery to a cardiac valve, comprising: a first support element with a collapsed delivery configuration and a deployed configuration; a second support element with a collapsed delivery configuration and a deployed configuration; a first bridging member extending from the first support element to the second support element, wherein the first bridging member has a delivery configuration and a deployed configuration; and a second bridging member extending from the first support element to the second support element, wherein the first bridging member has a delivery configuration and a deployed configuration, wherein the first and second bridging members extend radially inward from the first and second support elements in the deployed configurations.

In some embodiments the first and second bridging members extend from first and second discrete locations around the first and second support elements, and can symmetrically extend from the first and second support elements. The first and second bridging members can extend from the first and second support elements about 180 degrees from one another.

In some embodiments at least one of the first and second support elements has an annular shape.

In some embodiments the first and second bridging members each have a replacement valve engagement portion adapted to securely engage a replacement heart valve. The engagements portions can each have anchoring and/or a locking element adapted to securely lock with a portion of a replacement heart valve.

In some embodiments the first and second support elements are adapted to preferentially bend at least one location.

In some embodiments the first and second support elements each have a curved portion in their deployed configurations, wherein the curved portions are adapted to assume a tighter curved configuration in the collapsed delivery configurations.

In some embodiments the first and second bridging members are generally C-shaped in their deployed configurations.

In some embodiments the first support element has at least one coupling element adapted to reversibly couple to a delivery system. The at least one coupling element can be a threaded bore.

In some embodiments the second support element has a dimension in the deployed configuration that is larger than a dimension of the first support element in the deployed configuration with or without one or more fixation elements attached and radially engaging in cardiac tissue when needed.

One aspect of the disclosure is a system adapted for endovascular delivery to replace a mitral valve, comprising: a cardiac valve support comprising a first support element with a collapsed delivery configuration and a deployed configuration; a second support element with a collapsed delivery configuration and a deployed configuration; a first bridging member extending from the first support element to the second support element, wherein the first bridging member has a delivery configuration and a deployed configuration; and a second bridging member extending from the first support element to the second support element, wherein the first bridging member has a delivery configuration and a deployed configuration; wherein the first and second bridging members extend radially inward from the first and second support elements in the deployed configurations; and a replacement heart valve comprising an expandable anchor and a plurality of leaflets adapted to be secured to the cardiac valve support.

In some embodiments the bridging members are adapted to securingly engage the replacement heart valve.

One aspect of the disclosure is a method of replacing a patient's mitral valve, comprising: endovascularly delivering a valve support to a location near a subject's mitral valve, the valve support comprising a first support element, a second support element, and first and second bridging members extending from the first and second support elements; expanding the first support element from a collapsed configuration to a deployed configuration secured against cardiac tissue below the plane of the mitral valve annulus; expanding the bridge members from delivery configurations to deployed configurations positioned in general alignment with the coaptation points of the native mitral valve leaflets; and expanding the second support element from a collapsed configuration to a deployed configuration secured against left atrial tissue above the plane of the mitral valve annulus.

In some embodiments expanding the first support element comprises allowing the first support element to self-expand against cardiac tissue.

In some embodiments expanding each of the bridge members comprises allowing the bridge members to assume a deployed configuration in which they extend radially inward from the first and second support elements.

In some embodiments expanding the second support element against left atrial tissue comprises allowing the second support element to self-expand.

In some embodiments expanding the first support element comprises expanding the first support element towards a generally annularly shaped deployed configuration.

In some embodiments expanding the first support element comprises expanding the first support element secured against papillary muscles and chords attached to the native mitral valve, and can be done without displacing them.

In some embodiments native leaflets continue to function after expanding the second support element.

In some embodiments expanding the first support element occurs before expanding the second support element.

In some embodiments expanding the bridge members comprises allowing the bridge members to symmetrically extend from the first support element to the second support element.

In some embodiments expanding the bridge members comprises allowing the bridge members to extend from the first and second support elements about 180 degrees from one another.

In some embodiments expanding the second support element comprises expanding the second support element to the deployed configuration in which the second support element has a dimension larger than a dimension of the first support element in the deployed configuration. The second support element may have one or more fixation elements adapted to pierce into cardiac tissue.

In some embodiments the method further comprises securing a replacement mitral valve to the valve support. Securing the replacement mitral valve to the valve support can include comprise expanding the replacement mitral valve from a collapsed delivery configuration to an expanded configuration. Expanding the replacement mitral valve can include expanding the replacement mitral valve with a balloon and/or allowing the replacement mitral valve to self-expand. Securing a replacement mitral valve to the valve support can comprise securing the replacement mitral valve radially within the valve support. Securing a replacement mitral valve to the valve support can comprise locking a replacement mitral valve element with a valve support element to lock the replacement mitral valve to the valve support. The bridge members can each comprise a bridge lock element and the replacement mitral valve can comprise a plurality of lock elements such that the locking step comprises locking one of the plurality of lock elements with one of the bridge lock elements and locking a second of the plurality of lock elements with the other of the bridge lock elements.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 5A-5D illustrate an exemplary delivery system for delivering a replacement mitral valve support structure.

DETAILED DESCRIPTION OF THE DISCLOSURE

The disclosure is generally related to cardiac valve support structures that are adapted to be implanted near or within a native cardiac valve or native valve annulus and are adapted to provide support for a replacement heart valve. The support structures are adapted to interact with a replacement heart valve to secure it in an implanted position near or within the native valve or native valve annulus. In some embodiments the support structure is adapted to be positioned near or within the mitral valve annulus, and is adapted to interact with a subsequently delivered replacement mitral valve to secure the replacement mitral valve in place to replace the function of the native mitral valve.

The disclosure also provides for two-step endovascular implantation procedures for replacing a patient's native mitral valve. In general, a support structure is first positioned near or within a mitral valve annulus and secured in place. A replacement mitral valve is subsequently secured to the support structure, securing the replacement valve in place near or within the annulus. By implanting the support structure and replacement mitral valve in two steps, the replacement mitral valve can have a lower delivery profile because it does not have to expand as much to contact native tissue due to the presence of the support structure. This eliminates the need to have a large delivery profile replacement valve as would be required if attempting to position an aortic valve in the native mitral valve, or if attempting to position a one-piece mitral valve implant (i.e., an implant not assembled in-vivo) within the native mitral valve.

Figure 1A:
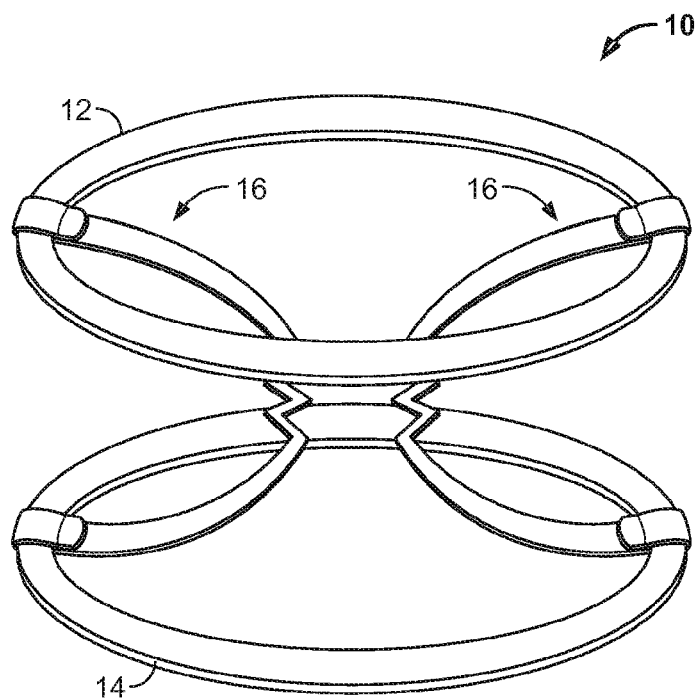
FIGS. 1A-1C illustrate an exemplary replacement mitral valve support structure in an expanded configuration.
Figure 1B:
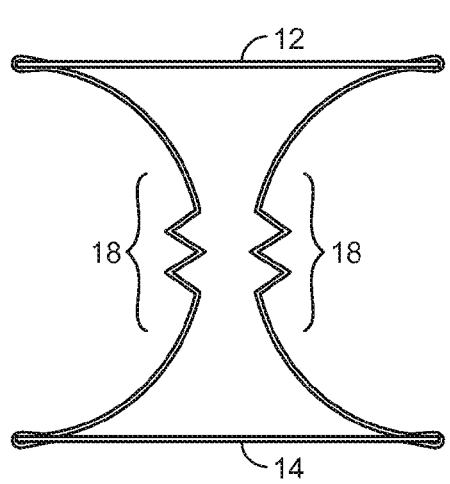
Figure 1C:
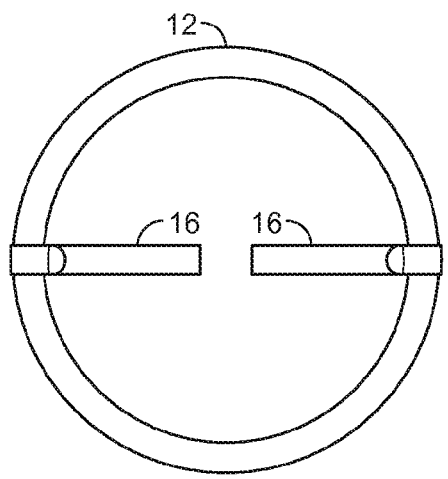

FIGS. 1A-1C illustrate an exemplary embodiment of a valve support in an expanded configuration. Valve support 10 includes a first support element 12, a second support element 14, and first and second bridge members 16 extending from first support 12 to second support 14. FIG. 1A illustrates a perspective view of valve support 10, while FIGS. 1B and 1C illustrate a side view and top-view, respectively, of valve support 10. As shown in FIG. 1B, each of bridge members 16 includes a valve engaging portion 18.

In some embodiments the first support element and the second support element are generally annular in shape in their expanded configurations (see, for example, FIG. 1A). Patient-to-patient variability in the cardiac anatomy can, however, require that the support elements have a variety of sizes and configurations. The support elements can therefore have any configuration as needed to be secured to any anatomical configuration. For example, the support elements can have generally elliptical configurations. Additionally, the support elements need not have the same general configuration. For example, the superior support element can have a generally annular shape and the inferior support element can have a generally elliptical shape. The bridge members operably connect the first and second support elements, and extend generally radially inward and axially away from a first of the support elements before extending radially outward towards the second of the support elements. For example, in the embodiment in FIGS. 1A-1C, bridge member 16 extends from support 12 in a radially inward direction and axially away from support element 12 and towards support element 14, before extending radially outward towards support 14.

The valve engaging portions of the bridge members are disposed radially inward relative to the support elements. The bridge members are biased to the configurations shown in FIGS. 1A-1C, with the valve engaging portions disposed radially inward relative to the support elements. Because they are biased towards this configuration, they are adapted to apply a radially inward force to a subsequently positioned replacement mitral valve that is expanded to an expanded configuration within the bridge members (described below). The bridge members are therefore adapted to engage the replacement heart valve to secure the replacement mitral valve to the valve support.

In the embodiment in FIGS. 1A-1C, the bridge members extend from the support elements at discrete locations around the support elements. That is, in this embodiment, the bridge members do not extend from the support elements all the way around the support elements. If they did, the valve support would have a general hourglass shape. The bridge members, therefore, are not complete extensions of the support elements. While the embodiment in FIG. 1A-1C shows two bridge members extending from the support elements at discrete locations, the valve support may include more than two bridge members extending from the support elements at discrete locations along the support elements.

In the embodiment in FIGS. 1A-1C, the bridge members also symmetrically extend from the first and second support elements. That is, there is at least one line or plane extending through the valve that, in at least one view of the valve support, creates portions of the valve support that are symmetrical. For example, in reference to FIG. 1C, a line extending through and connecting the bridge members creates symmetrical portions of the valve support. Or, for example, in reference to FIG. 1B, a vertical line extending through the center of the valve support creates symmetrical portions of the valve support.

In some embodiments the first and second support elements and the bridge members are made from a resilient material that can be deformed into a delivery configuration yet are adapted to self-expand to an expanded configuration, with optional additional expansion of one or more components by balloon dilation. For example, the support can be made from Nitinol, relying on its superelastic properties. In some embodiments the valve support is made from a material with shape memory properties, such as nitinol, and is adapted to return to an expanded memory configuration after being heated above its transition temperature. In some embodiments in which the valve support is made from a material such as nitinol, the shape memory properties and the superelastic properties are utilized. In the embodiment in FIGS. 1A-1C, valve support 10 is adapted to return to the expanded configuration shown, either by self-expansion (relying on the superelasticity of the material), or by being heated above its transition temperature (such as by exposure to the body's temperature).

Once the support structure is expanded and secured in place within the native mitral valve, a replacement mitral valve in a collapsed delivery configuration is advanced through the first support structure and positioned within the bridge members. Expansion of the replacement mitral valve (e.g., balloon expansion, self-expansion, etc.) not only expands the replacement mitral valve, but applies an expanding force on the bridge members, expanding them further radially outward towards the native annulus. Expansion of the replacement mitral valve causes the replacement valve to engage the bridge members and secure the replacement mitral valve to the valve support. Because the bridge members are biased towards a configuration in which they extend generally radially inward, the bridge members apply a radially inward force on the replacement mitral valve, helping to secure the replacement mitral valve in place. Further details of exemplary deployment procedures are described below.

In the embodiment shown in FIGS. 1A-1C, the bridge members and support elements are separate and distinct elements secured to one another by any suitable technique (e.g., soldering). In some alternative embodiments, the support elements and the bridge members are manufactured as a single unit without components that need to be secured to one another (see, for example, the exemplary embodiments in FIGS. 3A-7 below). For example, in some embodiments the manufacturing of the valve support is simplified because it is manufactured from a single tubular shape memory material that is pre-formed with predetermined expansion ratios and forces needed to retain the replacement mitral valve in place.

In some embodiments the height of the valve support, measured from the base of the first support to the top of the second support, is about 1 cm to about 50 cm to be able to accommodate the height of the replacement heart valve, such as a stented heart valve. In some embodiments the height is greater than 50 cm. In some embodiments the height of the valve support is between about 10 cm and about 25 cm. For example, a stented heart valve in an expanded configuration can have a height of about 17.5 mm. In some embodiments, however, the height of the valve support is less than the height of the replacement heart valve. These numbers are merely exemplary and are not limiting. Additionally, the two annular support elements can have different dimensions. For example, the two support elements, if generally annular-shaped, can have different diameters. In some embodiments the first support element has a larger diameter than the second support element because the anatomical position in which it is to be placed is larger than the anatomical position in which the second support element is to be placed. In the embodiment shown in FIGS. 1A-1C, support element 12 can have a larger diameter than support element 14 due to its expansion in the larger left atrium versus the smaller left ventricle, the papillary tendons and muscles, and other supporting structures in the left ventricle. The possible differences in dimensions of the superior and inferior support elements are discussed in more detail below.

In the embodiments described herein the support elements do not have a covering element. In some embodiments, however, one or more support elements can have a covering element such as a sealing skirt to enhance the sealing of blood flow in and around the support structure and replacement heart valve. The covering element can be any type of material that surrounds the support elements and provides the enhanced sealing functionality.

In some embodiments one or more of support structures is covered in a material such as a polyester fabric (e.g., Dacron). Alternatively or in addition to, one or more of the bridge members can be covered in a polyester fabric such as Dacron.

Figure 2A:
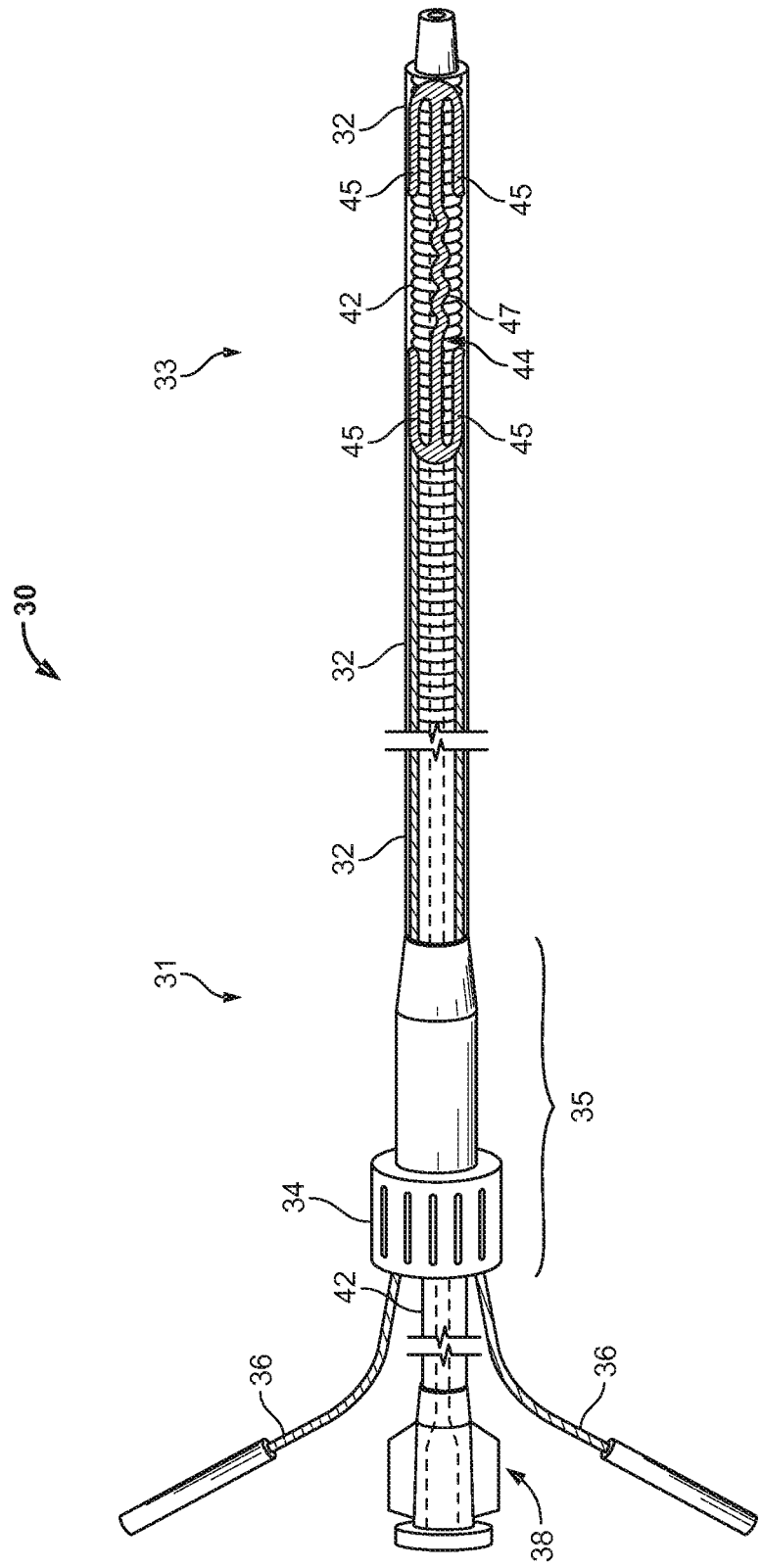
FIGS. 2A-2C illustrate an exemplary delivery system for delivering a replacement mitral valve support structure.
Figure 2B:
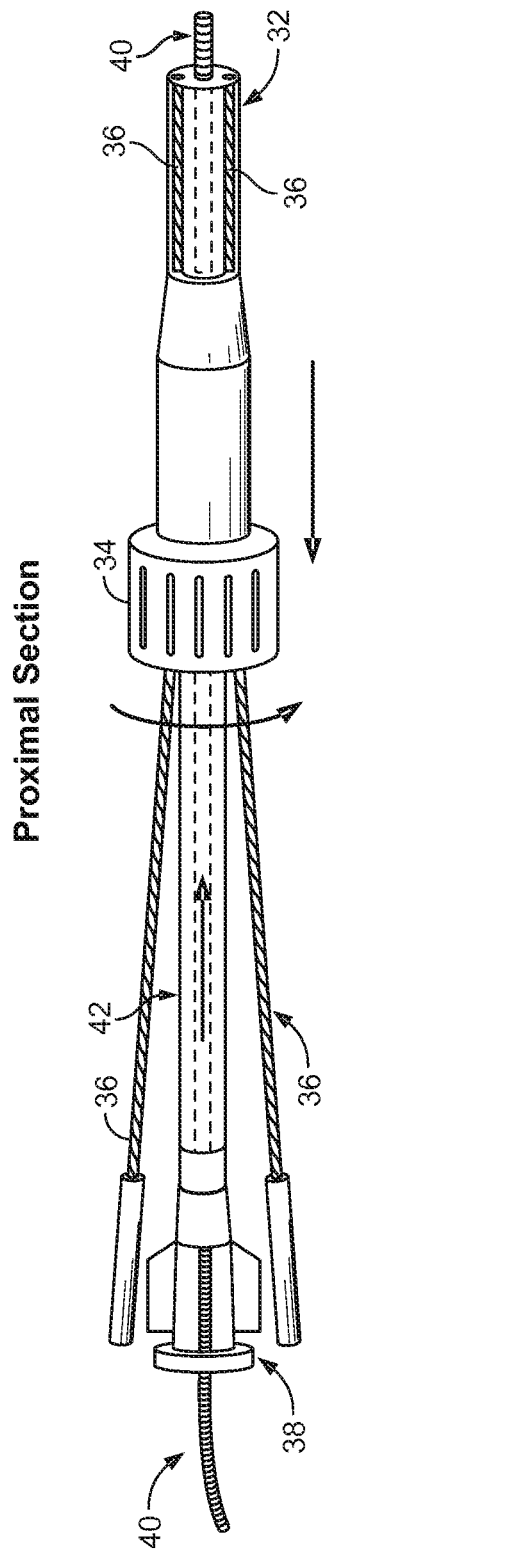
Figure 2B:
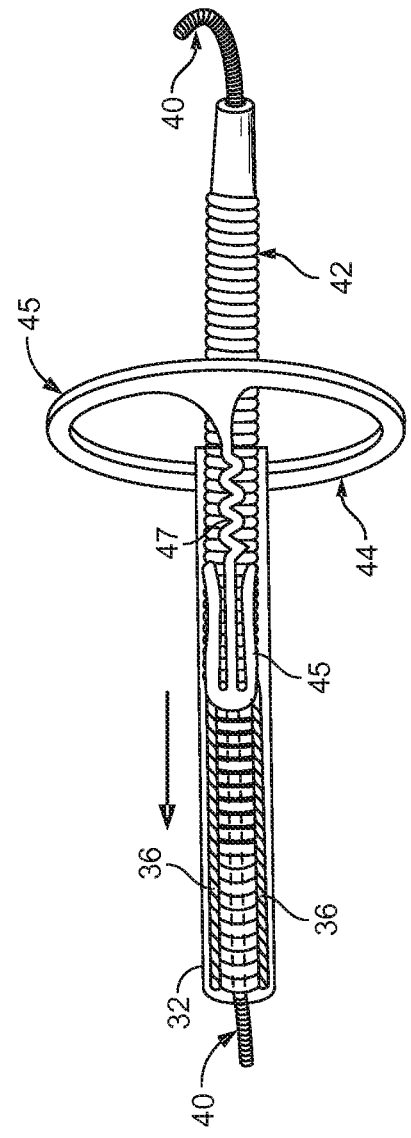

FIG. 2A illustrates an exemplary delivery device and mitral valve support therein in a collapsed delivery configuration. Delivery device 30 includes actuation portion 35 that includes actuator 34. Delivery device 30 also includes elongate body 32, which is secured to actuation portion 35. Delivery device 30 also includes guidewire lumen 42 coupled to luer 38, wherein lumen 42 is adapted to be advanced distally over guidewire 40 (see FIG. 2B) to advance delivery device 30 to a target location within the subject. The portion of delivery device 30 to the left of the broken lines can be considered the proximal portion of delivery device 30, at least a portion of which remains external to the patient during the procedure, providing a user access to actuation portion 35. The portion of the device to the right of the broken line can be considered the distal portion, and is generally considered the portion of the delivery device adapted to be advanced through a patient during the procedure. Actuator portion 35 includes actuator 34 that is adapted to be actuated to control the movement of elongate body 32. Specifically, actuation of actuator 34 controls the axial (i.e., proximal and distal) movement of elongate body 32 relative to inner lumen 42 and to valve support 44. In FIGS. 2A and 2B, rotation of actuator 34 controls the relative axial displacement of elongate body 32, but any other suitable type of actuator can be used and incorporated into the system to control the axial displacement of elongate body 32. Lumen 42 is axially displaceable relative to elongate body 32 by axial movement of the proximal end of lumen 42. Delivery device 30 also includes device coupling members 36, which extend out of the proximal end of the proximal portion of device 30, and also extend distally radially within elongate body 32 yet external to guiding lumen 42. The distal regions of device coupling members 36 are releasably secured to valve support 44 during the deployment procedure (as shown in FIGS. 2A and 2B), but are also adapted to be controllably released from valve support 44 to release the valve support from the delivery device. Coupling members 36 can be actuated by actuating their proximal portions external to the patient to control movement of valve support 44. In FIG. 2A valve support 44 is in a collapsed delivery configuration within elongate body 32 and disposed external to guiding lumen 42. In the delivery configuration, the annular portions 45 of valve support 44 are collapsed down upon bridge members 47 (only one bridge member shown). When collapsed, roughly each half of an annular support 45 is collapsed down and has a C-shaped configuration with a tighter curved configuration (i.e., a portion with a smaller radius of curvature) than when in the expanded configuration (also see the delivery configuration of the valve support shown in FIG. 2C). When in the delivery configuration, bridge members 47 assume a straighter configuration than when in the expanded configuration. As described in more detail below, the annular support elements can be biased to bend at certain locations to ease their collapse during the loading process and during any recollapsing that may be needed. The axial position of the collapsed valve support is controlled by coupling members 36. FIG. 2B illustrates a portion of the process for releasing valve support 44 from delivery device 30 (more details of which are described below). Actuation of actuator 34, shown as rotation of actuator 34, causes elongate body 32 to retract in the proximal direction. Guiding lumen 42 can be maintained in position or advanced distally while the elongate body 32 is retracted. The relative movement between elongate body 32 and coupling members 36 (to which valve support 44 is attached) allows valve support 44 to begin to expand as elongate body 32 is moved proximally. In FIG. 2B, a first of the valve support's elements (and a small portion of bridge members 47) has expanded. Continued retraction of elongate body allows valve support 44 to fully expand, yet still be coupled to coupling members 36.

Figure 2C:
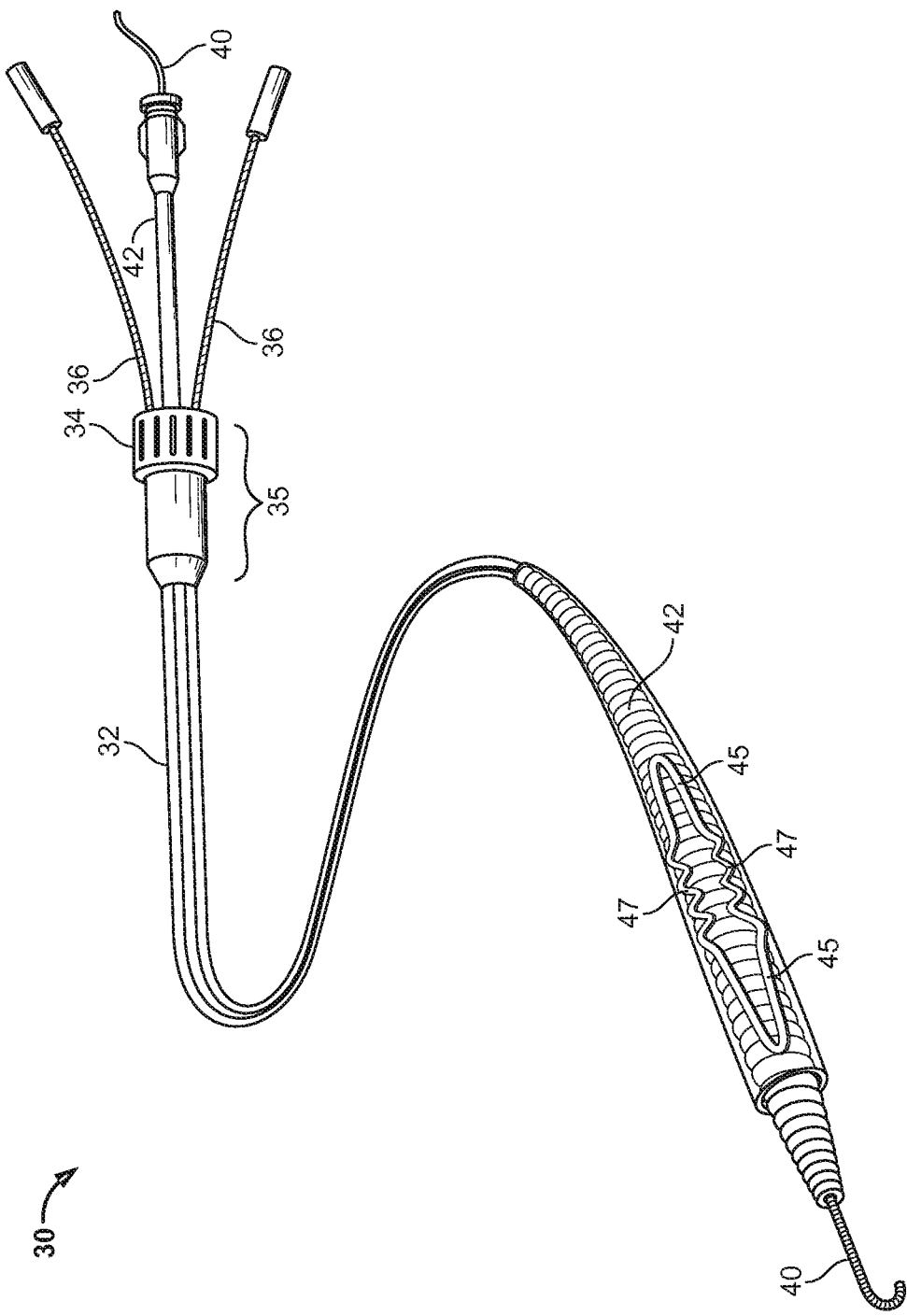

FIG. 2C illustrates an alternative perspective view of delivery device 30, illustrating both of the bridging members 47. In FIG. 2C, however, support elements 45 are adapted to deform generally axially away from the ends of the bridging members when collapsed within elongate body 32 in the delivery configuration.

In the embodiments in FIGS. 2A-2C, elongate body 32 can be, for example without limitation, a catheter, examples of which are well known. Actuation portion 35 can be, for example without limitation, a touhy borst, allowing rotation of actuator 34 to control the axial movement of elongate body 32. Guiding lumen 42 can be, for example without limitation, a corrugated steel reinforced lumen to allow for sufficient flexibility while being advanced through the vasculature. Guiding lumen 42 can also be any other type of suitable guiding lumen.

Access to the mitral valve or other atrioventricular valve will preferably be accomplished through the patient's vasculature percutaneously (access through the skin). Percutaneous access to a remote vasculature location is well-known in the art. Depending on the point of vascular access, the approach to the mitral valve can be antegrade and require entry into the left atrium by crossing the interatrial septum. Alternatively, approach to the mitral valve may be retrograde where the left ventricle is entered through the aortic valve. Alternatively, the mitral valve can be accessed transapically, a procedure known in the art. Additional details of an exemplary antegrade approach through the interatrial septum and other suitable access approaches can be found in the art, such as in U.S. Pat. No. 7,753,923, filed Aug. 25, 2004, the contents of which are incorporated herein by reference.

While the support structures herein are generally described as a support for replacement mitral valves, they can be delivered to a desired location to support other replacement cardiac valves, such as replacement tricuspid valves, replacement pulmonic valves, and replacement aortic valves.

Figure 3A:
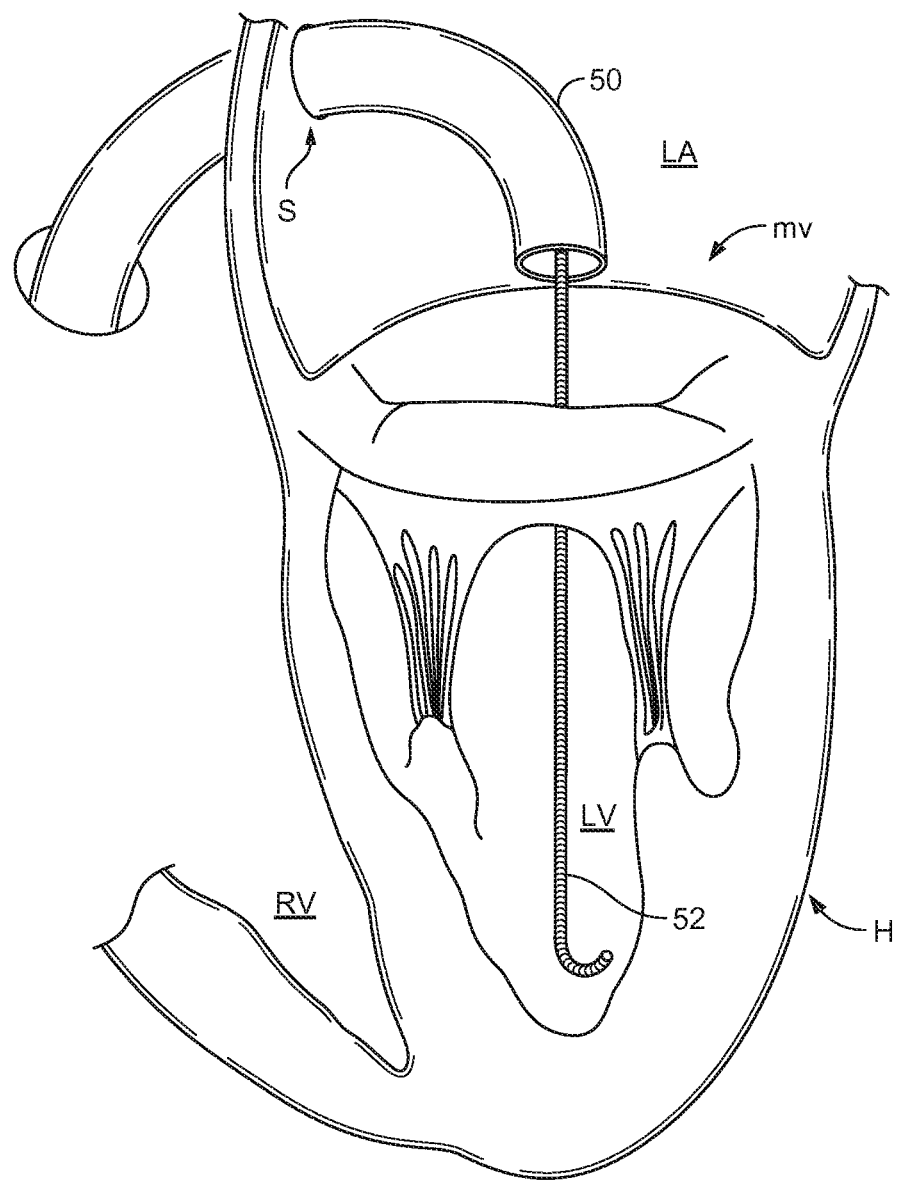
FIGS. 3A-3E illustrate an exemplary method of delivering and deploying an exemplary replacement mitral valve support structure.

FIGS. 3A-3E illustrate a section view of heart H, illustrating an exemplary method of deploying a valve support within a native mitral valve MV. Access to the mitral valve has been gained using a known approach through the femoral vein, IVC, right atrium, across the interatrial septum S, and into the left atrium LA. Exemplary details of such an approach can be found in, for example, without limitation, U.S. Pat. No. 7,753, 923. As shown in FIG. 3A, guide catheter 50 (e.g., an 18 F guide catheter) has been advanced over guidewire 52 through septum S to provide access to the mitral valve. Guidewire 52 has been advanced through the native mitral valve and into the left ventricle to allow the delivery device to be advanced over guidewire 52 and into position within the native mitral valve. Alternatively, guide catheter 50 can be advanced over guidewire 52 into position, and guidewire 52 can then be removed. The delivery device can then simply be advanced through guide catheter 50 without the use of guidewire 52. Guidewire 52 may preferably be left in place, however, to allow a subsequently delivered replacement mitral valve to be advanced over the guidewire 52.

Figure 3B:
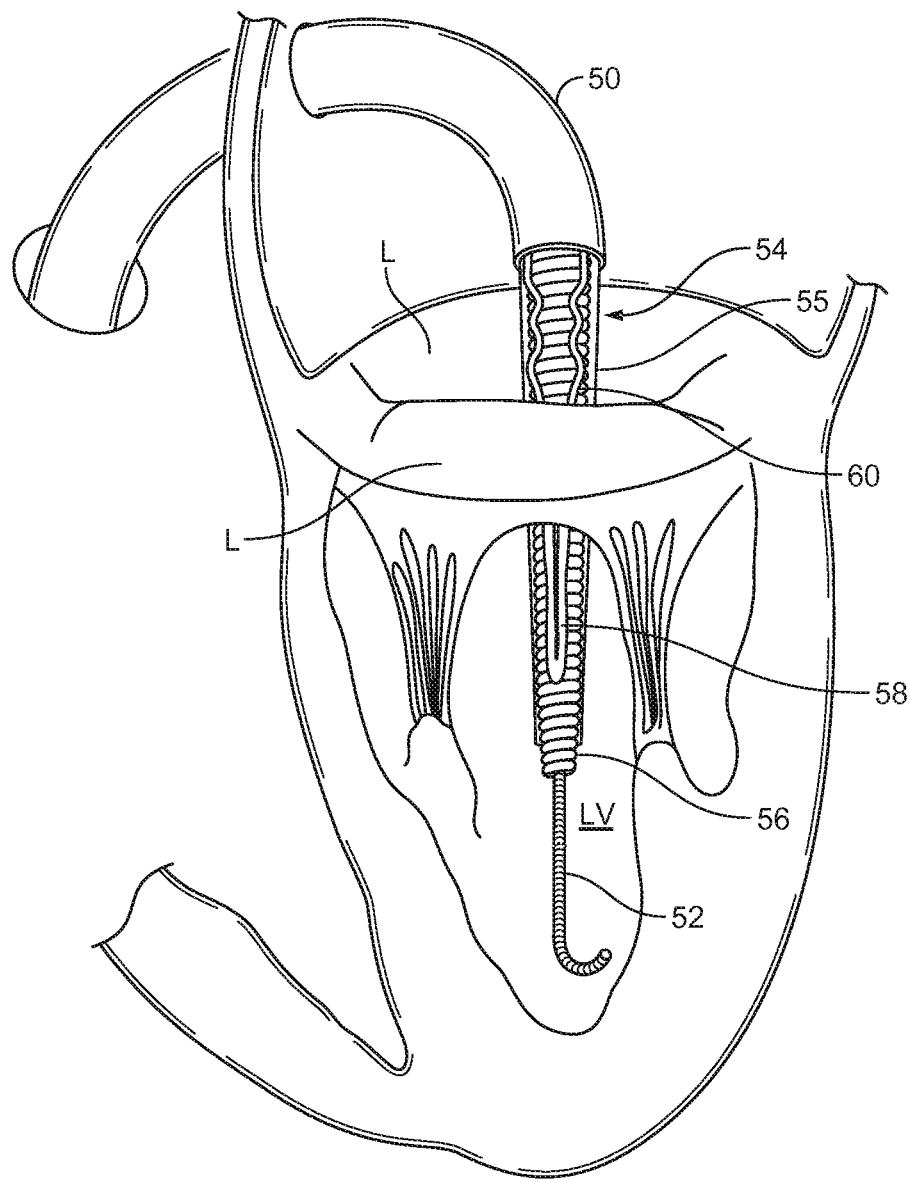

In FIG. 3B, delivery device 54 with a valve support collapsed therein has been advanced over guidewire 52 and through guide catheter 50, and out of the distal end of guide catheter 50. Delivery device 54 is advanced through the leaflets L of the native mitral valve, such that the distal end of elongate body 55 is disposed in the left ventricle LV, as shown in FIG. 3B.

Figure 3C:
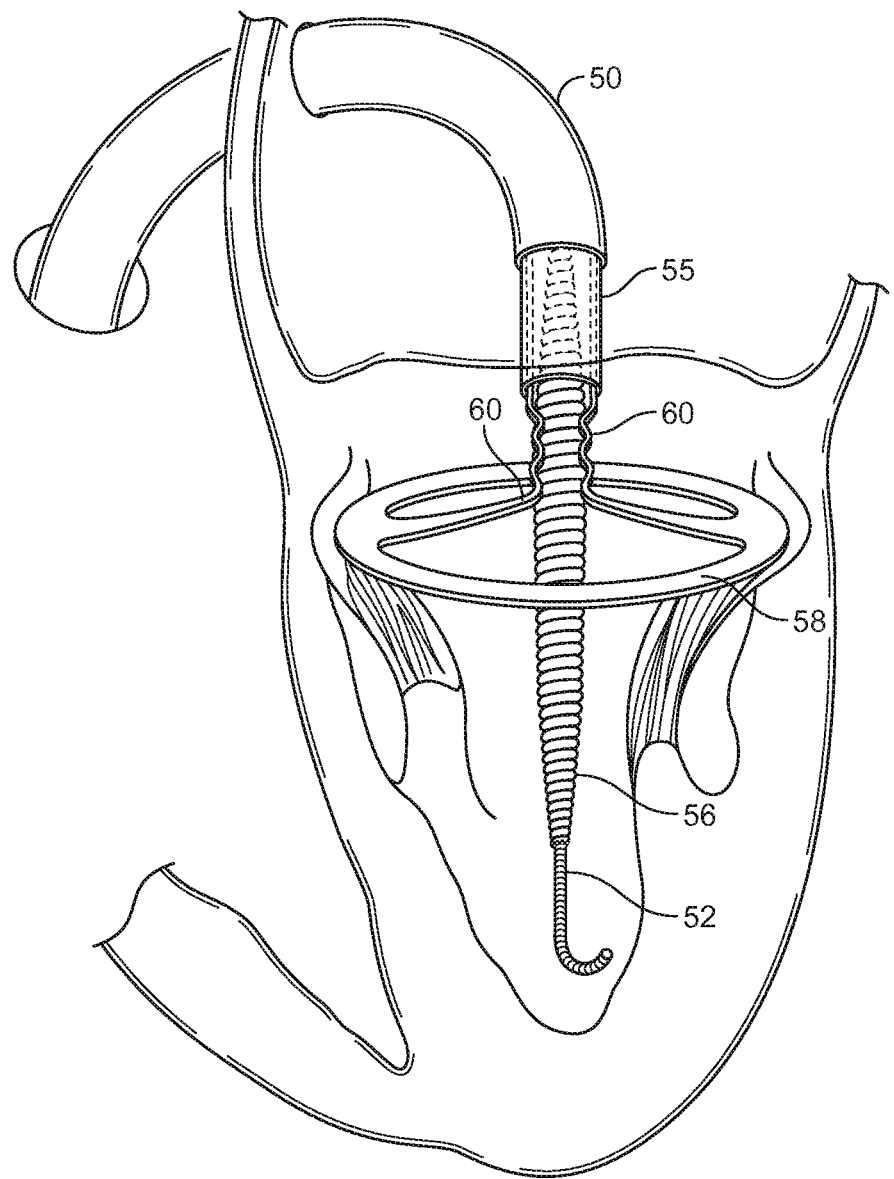
Figure 7:
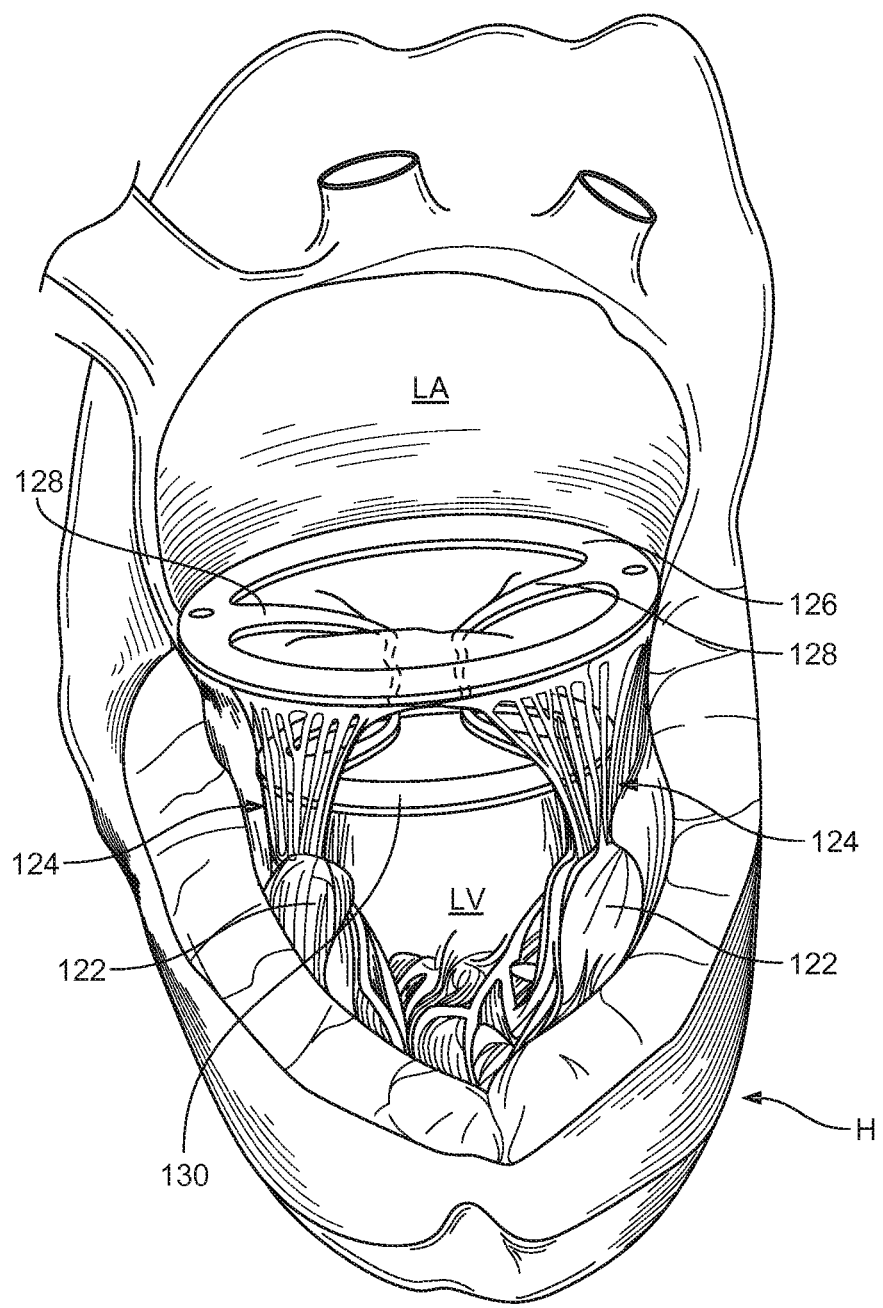
FIG. 7 illustrates an expanded valve support wherein the lower support element has a diameter that is smaller than the diameter of the upper support element.

As shown in FIG. 3C, elongate body 55 is then retracted proximally relative to the valve support, releasing the valve support from elongate body 55 (for example, using an actuator such as actuator 34 in FIGS. 2A-2C). In this embodiment, the valve support is made of a resilient material, such as nitinol, and begins to self-expand as elongate body 55 is retracted. In FIG. 3C, first support element 58 has self-expanded to the expanded annular configuration as shown. When support element 58 expands, it engages ventricular cardiac tissue below the plane of the mitral valve annulus, securing itself against tissue. Support element 58 is preferentially positioned in the sub-annular space, anchoring against the papillary muscles and chords with minimal or no damage to any of them so as not to interfere with their functioning. Support element 58 is preferably expanded distal enough such that native mitral valve leaflets can function even after expansion of support element 58. As discussed above, in some embodiments the lower, or inferior, support element has a smaller diameter than the upper, or superior, support element to match interpapillary distance as measured from the subject being considered. The smaller relative diameter provides the lower support element the ability to oppose the papillary tendons without displacing them. The tendons are attached at one end to the papillary muscles and at the other end to the native leaflets, and displacing the tendons or the muscles would prevent the native leaflets from properly closing, causing regurgitation during the expansion of the valve support. The lower support element is therefore secured in place without interfering with the function of the native leaflets. Referring briefly to FIG. 7, an exemplary valve support is shown expanded in place. Lower support element 130 is shown with a smaller diameter than upper support element 126. Support element 130 is opposed to tendons 124 but is not displacing them, and as such is not interfering with the function of papillary muscles 122 and tendons 124. Support element 130 is expanded in the sub-annular space, while support element 126 is expanded in the left atrium LA. While the embodiments shown herein may appear to show a lower support element that is displacing the tendons and/or papillary muscles, it is intended that the lower support is properly sized such that it is expanded in the manner shown in FIG. 7.

Referring back to FIG. 3C, elongate body 55 has been retracted proximally relative to a portion of bridge members 60, allowing a portion of bridge members 60 to expand. Support element 58 can be recollapsed back within elongate body 55 at this point in the procedure if necessary. The positioning of the valve support can be visualized using known visualization techniques (e.g., fluoroscopy, or any other imaging modalities as necessary) and if it is determined that support element 58 is not positioned properly, elongate body 55 can be advanced distally relative to the valve support, coupling members 64 can be retracted relative to elongate body 55, or a combination of the two can be performed to recollapse at least a portion of support element 58 back within elongate body 55. The valve support can then be repositioned, and support element 58 can then be re-expanded to secure proper placement in the desired anatomical position or space.

Figure 3D:
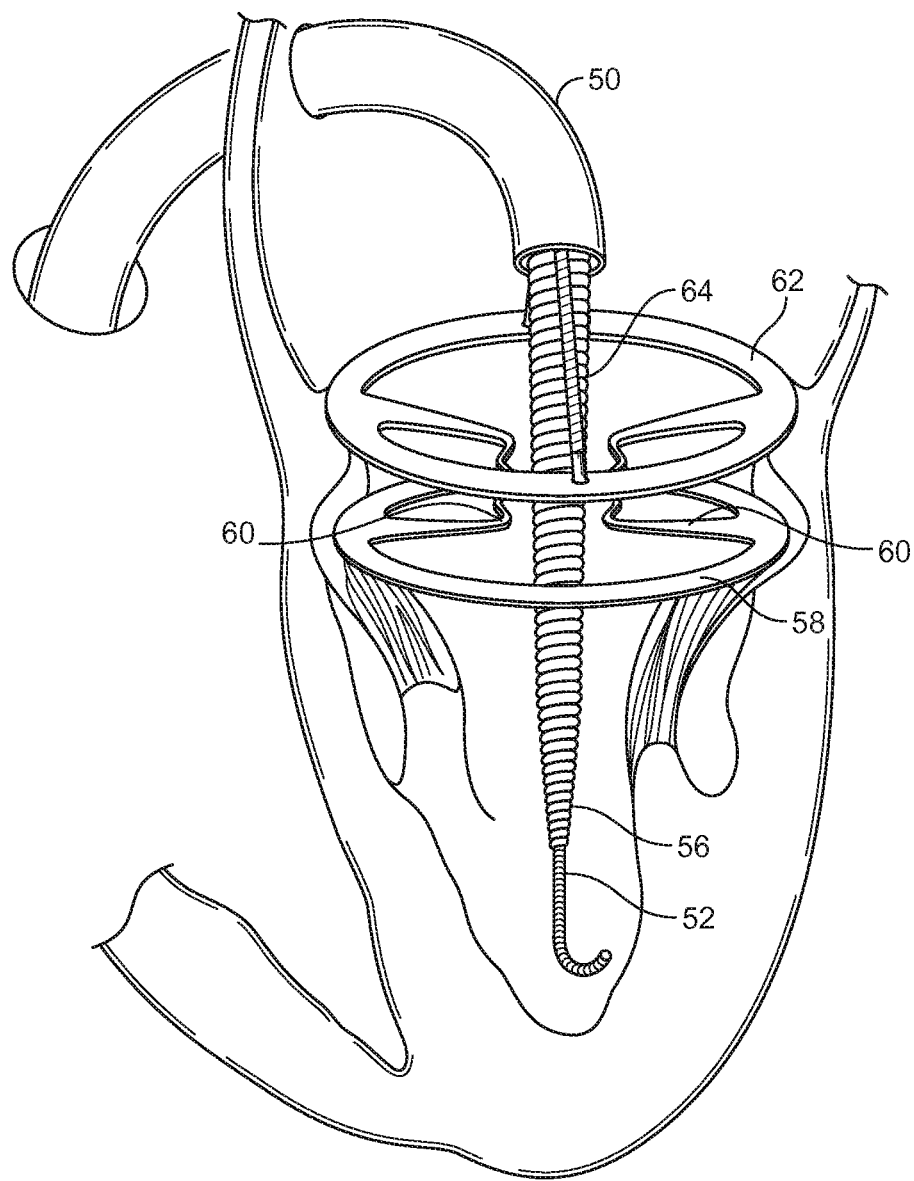

As shown in FIG. 3D, continued proximal retraction of elongate body 55 (not shown in FIG. 3D) allows the second support element 62 to self-expand, securing itself against the lateral wall of the atrium above the mitral valve annulus. In some embodiments the second support element includes one or more fixation elements, such as in the form of anchors, barbs, clips, etc., that help secure the second support element against cardiac tissue, or that are adapted to pierce into cardiac tissue to secure the support element to cardiac tissue. One or more fixation elements, if used, can be disposed around the periphery of the support element. They can assume a collapsed, or delivery configuration for delivery of the system, but can deploy to an expanded, or anchoring, configuration, when released from the delivery system. For example, the fixation elements can be an elastic material that self-expands to an anchoring configuration. Alternatively, the fixation elements can be actuated to reconfigure them to a fixation configuration. In some embodiments, however, the one or more fixation elements are not adapted to change configurations. The mitral valve leaflets are not shown in FIG. 3D for clarity. Coupling members 64 (only one can be seen in FIG. 3D) are still controllably secured to second support element 62. Support element 62 can be recollapsed back within elongate body 55 at this point in the procedure. This can occur as described above with respect to support element 58. In some embodiments support element 62 can be adapted to preferentially bend (for collapsing towards its delivery configuration) at or near the point at which coupling members 64 are secured. If it is determined that support element 62 should be recollapsed within elongate body 52, a proximally directed force can be applied to coupling members 64, thereby applying a force on support element 62. If support element 62 is adapted to preferentially bend at the location at which the coupling members are secured, the force will be applied at the location at which the support is adapted to preferentially bend. This will allow support element 62 to be deformed towards its collapsed configuration more easily and more efficiently. Once support element 62 is collapsed within elongate body 55, continued retracting of coupling members 64 can cause support element 58 to collapse as well. Support element 58, like support element 62, can be adapted to preferentially bend at certain locations, easing the deformation towards its delivery configuration.

The locations on support element 62 (and support element 58) from which bridge members 60 extend are roughly 180 degrees apart from one another, similar to the roughly 180 separation of the native leaflet coaptation points. In the expanded configuration shown in FIG. 3D, the locations on the support elements from which the bridge members extend are generally preferably positioned at the ends of the line of coaptation between the two native valve leaflets. That is, a line connecting the points on the support elements from which the bridge members extend is preferentially (although not necessarily) in alignment with the line of coaptation of the native valve leaflets. One or both support elements may have radiopaque markers at these locations to assist in proper orientation of the valve support in place. By positioning the bridge members in these locations relative to the native leaflets, the bridge members do not interfere with the functioning of the native valve leaflets during the implantation procedure (or at least interfere minimally), even after the valve support is deployed to the fully expanded configuration shown in FIG. 3D. Because the native leaflets can function during this part of the procedure, time is not a critical factor during the deployment of the valve support.

While the support structures herein are generally described as including two bridging elements, the support structures can be have more than two bridging elements disposed in any configuration around the support structures.

Figure 3E:
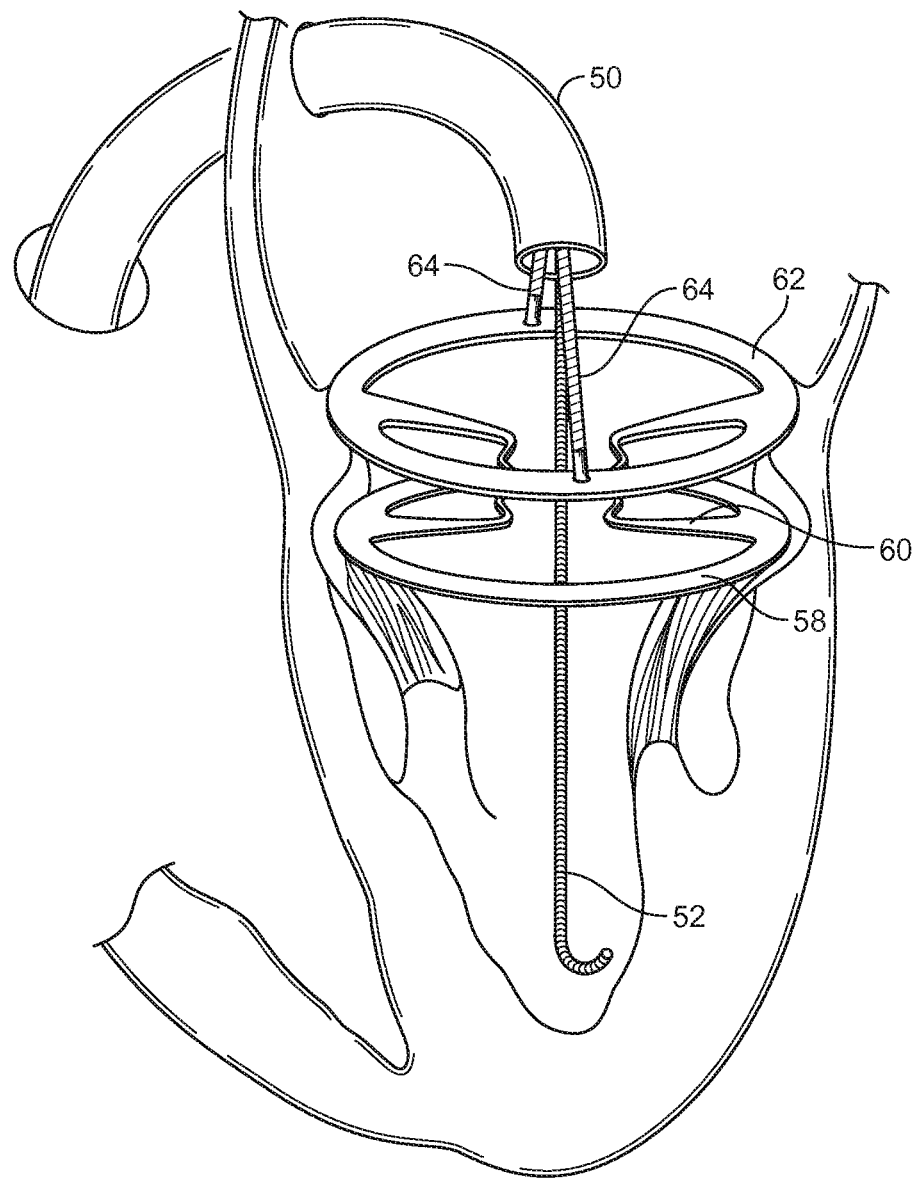

Next, guiding member 56 is retracted from the patient, leaving guidewire 52, guide catheter 50, and elongate body 55 in place, as shown in FIG. 3E. Guide catheter 50 and guidewire 52 can now provide access to the mitral valve to allow a replacement mitral valve to be secured to the valve support which has been expanded and secured within the native valve.

Figure 4A:
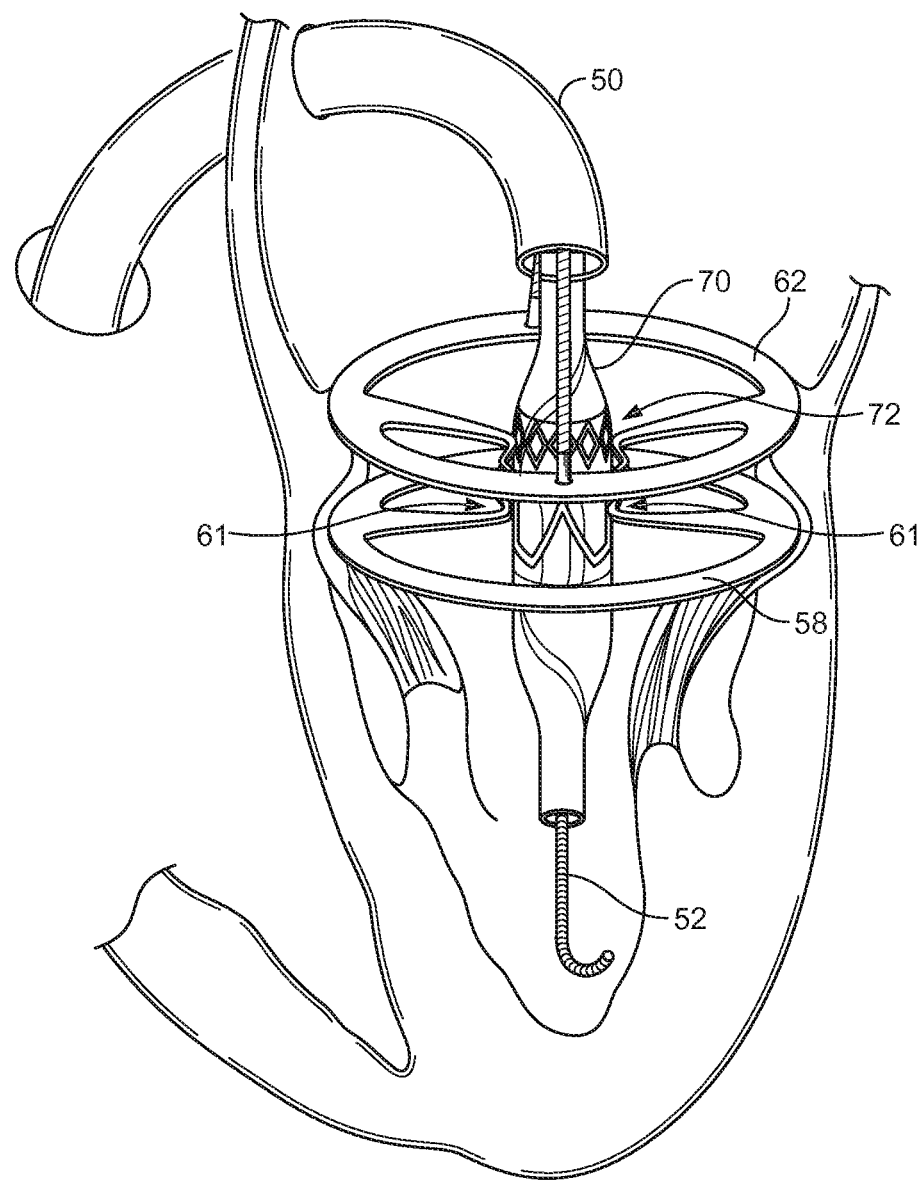
FIGS. 4A-4D illustrate an exemplary method of deploying a replacement mitral valve and securing it to a replacement mitral valve support structure.

FIGS. 4A-4D illustrate the subsequent delivery and expansion of an exemplary replacement mitral valve. In FIG. 4A, a balloon catheter with balloon 70, along with replacement valve 72 thereon, has been advanced over guidewire 52 and within guide catheter 50 to the position shown radially within the expanded valve support. In general, replacement valve 72, which in this example comprises an expandable stent and replacement leaflets secured thereto, is advanced until it is positioned radially within valve engagement portions 61 of the bridge members. Once the replacement valve is determined to be in an optimal position across the atrio-ventricular line (e.g., using a visualization technique such as echocardiogram), the replacement valve can be expanded.

Figure 4B:
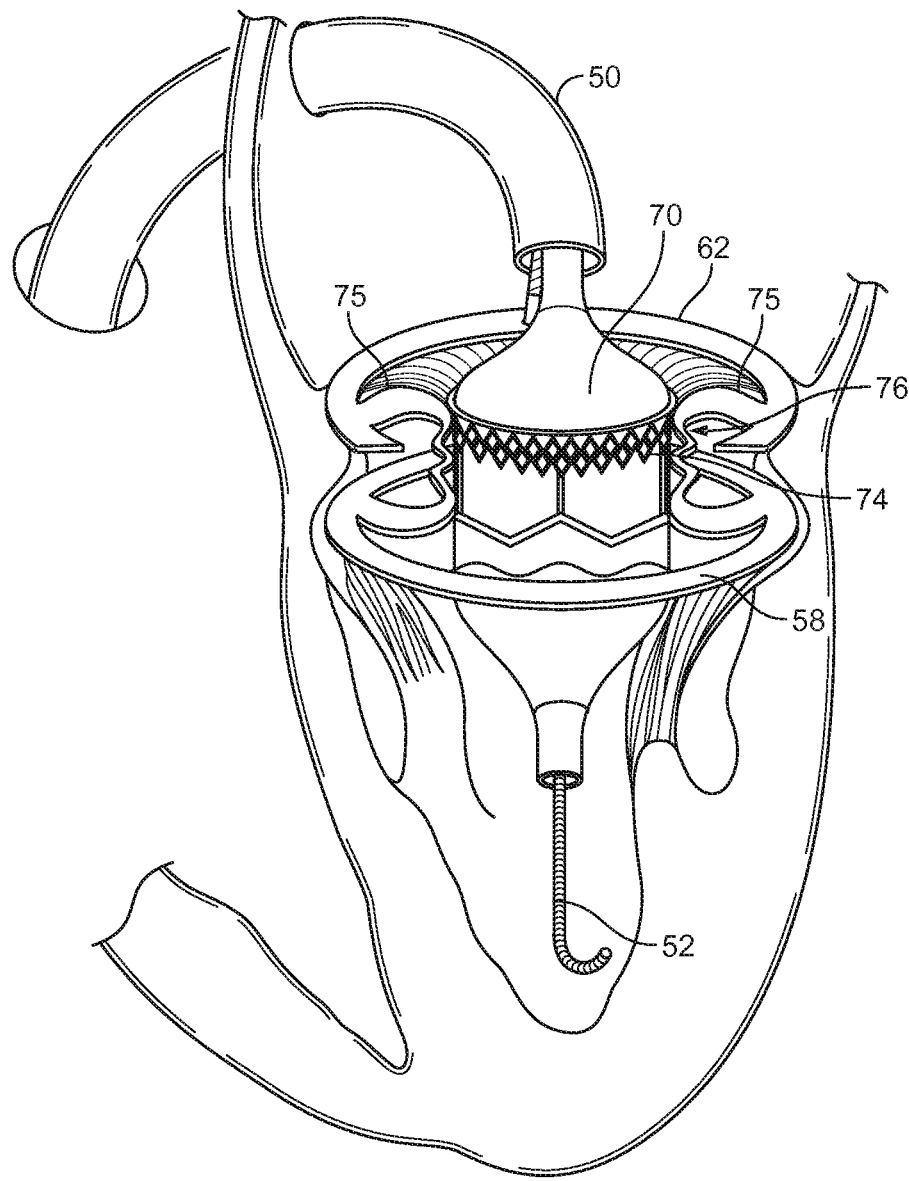

As shown in FIG. 4B, balloon 70 is expanded by filling it with an expansion fluid, a procedure known in the art. Expansion of balloon 70 expands the expandable stent portion of the replacement valve. Expansion of the stent applies radially outward forces on the bridge members of the valve support, causing them to expand (or rather, deform in a general radially outward direction). As the stent expands, the stent pushes the native leaflets outward towards the annulus. As the stent expands, apertures in the stent defined by the stent material are adapted to engage with protrusions or other surface features of the valve engagement portion of the bridge members to secure the expandable stent to the bridge members. The radially inward bias of the bridge members also helps secure the replacement valve within the valve support by applying a radially inward securing force on the stent. The stent is applying a radially outward force on the bridge members as well, and the two interact to allow the replacement valve to be secured in place, preventing the replacement valve from being displaced axially as well as from being collapsed. Additionally, the bridge members can be adapted to assume a preferential expanded configuration (such as is shown in FIG. 4B) when expanded replacement valve expansion process. For example, the bridge members can be adapted to have bending points 75 at which the bridge members will preferentially bend when expanded, which will prevent the two support members from migrating axially away from one another during the replacement valve expansion process. Bending points 75 can also assist in securing the replacement valve relative to the support structure.

Figure 4C:
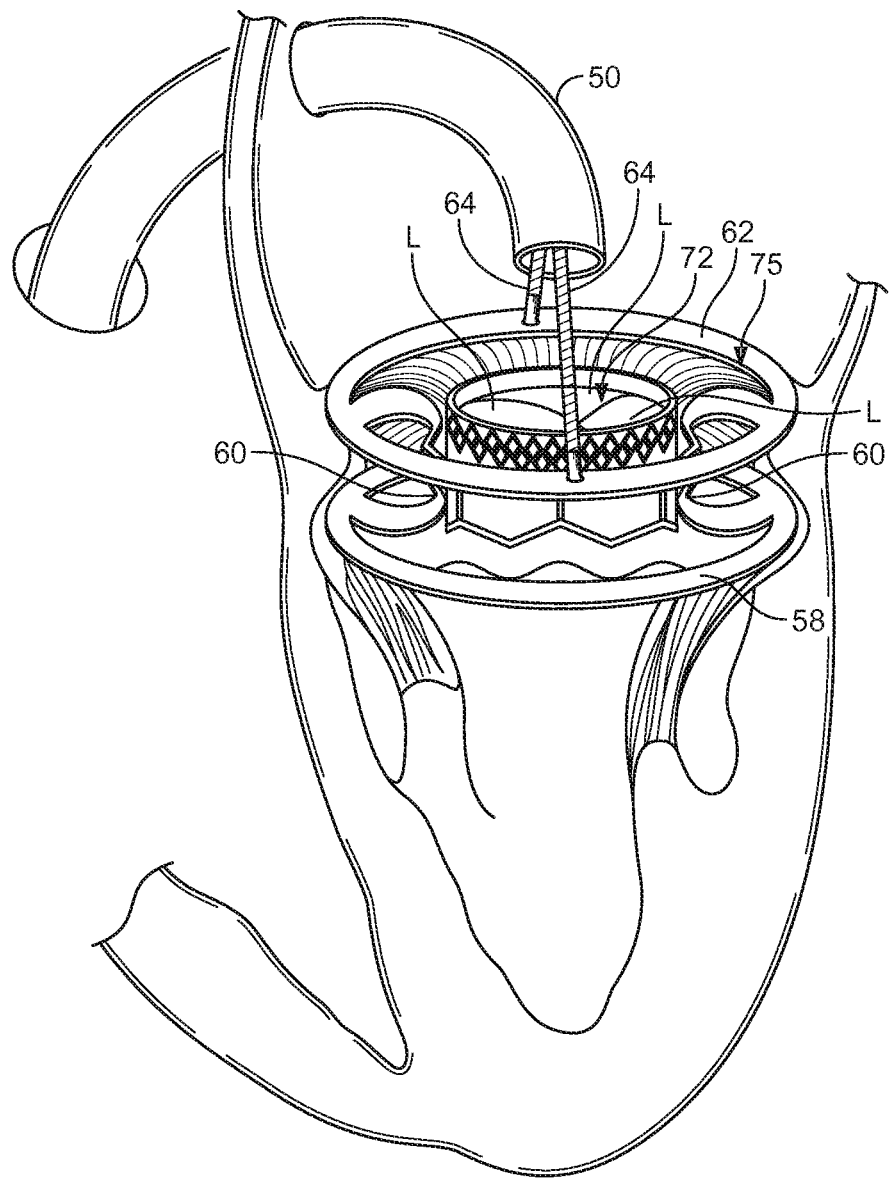

After the replacement valve has been expanded and secured in place, balloon 70 is deflated and withdrawn, along with the guidewire, from the patient, as is shown in FIG. 4C. Once the balloon is deflated, the leaflets L of the replacement mitral valve begin to function. Three leaflets are shown to illustrate that known replacement aortic valves, mere examples of which are described in U.S. Pat. No. 7,585,321, filed May 27, 2005, can be used in this exemplary procedure to replace the native mitral valve.

While a balloon expandable replacement heart valve has been shown, the replacement heart valve can be self-expanding as well.

Figure 4D:
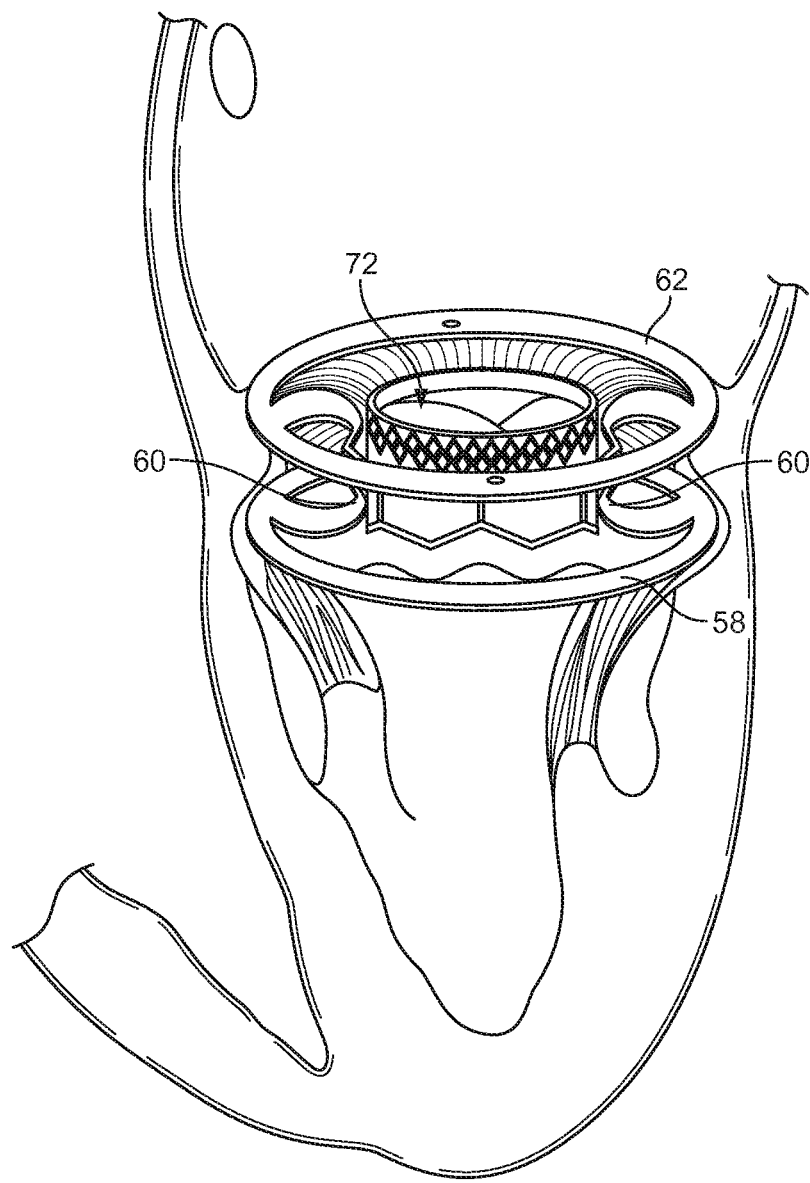

Once the replacement valve is secured in place within the valve support, coupling members 64 are disengaged from support element 62. In this exemplary embodiment the distal ends of coupling members 64 have threads which adapted to engage threaded bores within support element 62. Rotation of coupling members 64 causes the coupling members 64 to be unscrewed from support element 62, thereby uncoupling the coupling members 64 from support 62. Guide catheter 50 is then removed from the patient, leaving the implant in place, as shown in FIG. 4D.

As set forth above, the mitral valve can be accessed via a transapical approach, or though the apex of the heart. In such an approach, coupling members 64 would be secured to inferior support element 58 rather than superior support element 62, as shown in the embodiments herein. The coupling members 64 could still be actuated in the same manner as described herein.

FIGS. 5A-5D illustrate an exemplary delivery device and mitral valve support therein in a delivery configuration. The delivery device and mitral valve support are similar to those shown in the embodiments in FIGS. 2A-2C. Delivery device 80 includes hemostasis valve 82 comprising rotating male luer lock 81 and female luer sideport 83. Delivery device 80 also includes elongate body 84 secured to actuator 85, wherein actuator 85 is adapted to be rotated to control the axial movement of elongate body 84. Device 100 is collapsed within elongate body 84 and is disposed radially outward relative to lumen 86. Delivery device 80 also includes guidewire lumen 86, which is adapted to receive guidewire 90 therein, coupled to luer 88, which are adapted to move axially relative to elongate body 84. Coupling members 92 are reversibly secured to valve support 100 as set forth in the embodiments above. Other details of delivery device 80 can be the same as those described in the embodiments above.

In FIG. 5B, actuation of actuator 85 causes proximal retraction of elongate body 84 relative to valve support 100. This causes distal support element 101 of valve support 100 to begin to self-expand to a deployed configuration against tissue (anatomy not shown for clarity), such as in the embodiment in FIG. 3A-3E. Hemostasis valve 82 can alternatively, or in addition to, be pulled proximally (as indicated in by the arrow in FIG. 5B) to cause elongate body 84 to retract relative to valve support 100. In addition, or alternatively, guiding lumen 86 can be advanced distally (as indicated by the arrow in FIG. 5B) relative to elongate body 84. These types of motion can cause or assist in the expansion of the valve support.

Figure 5A:
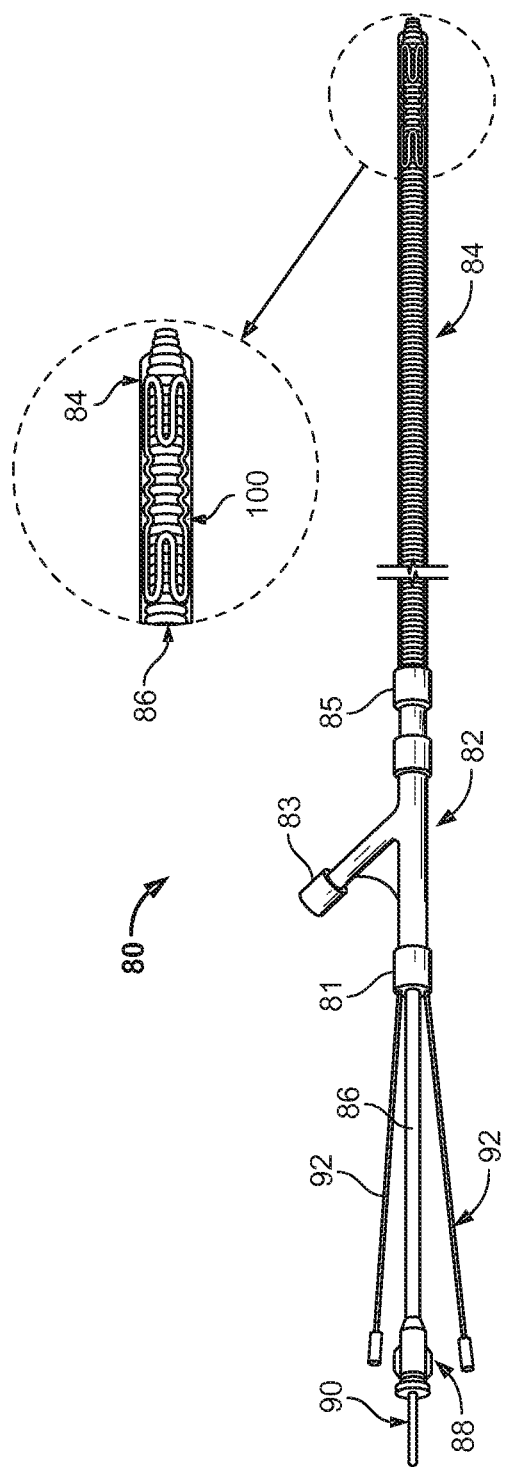
Figure 5C:
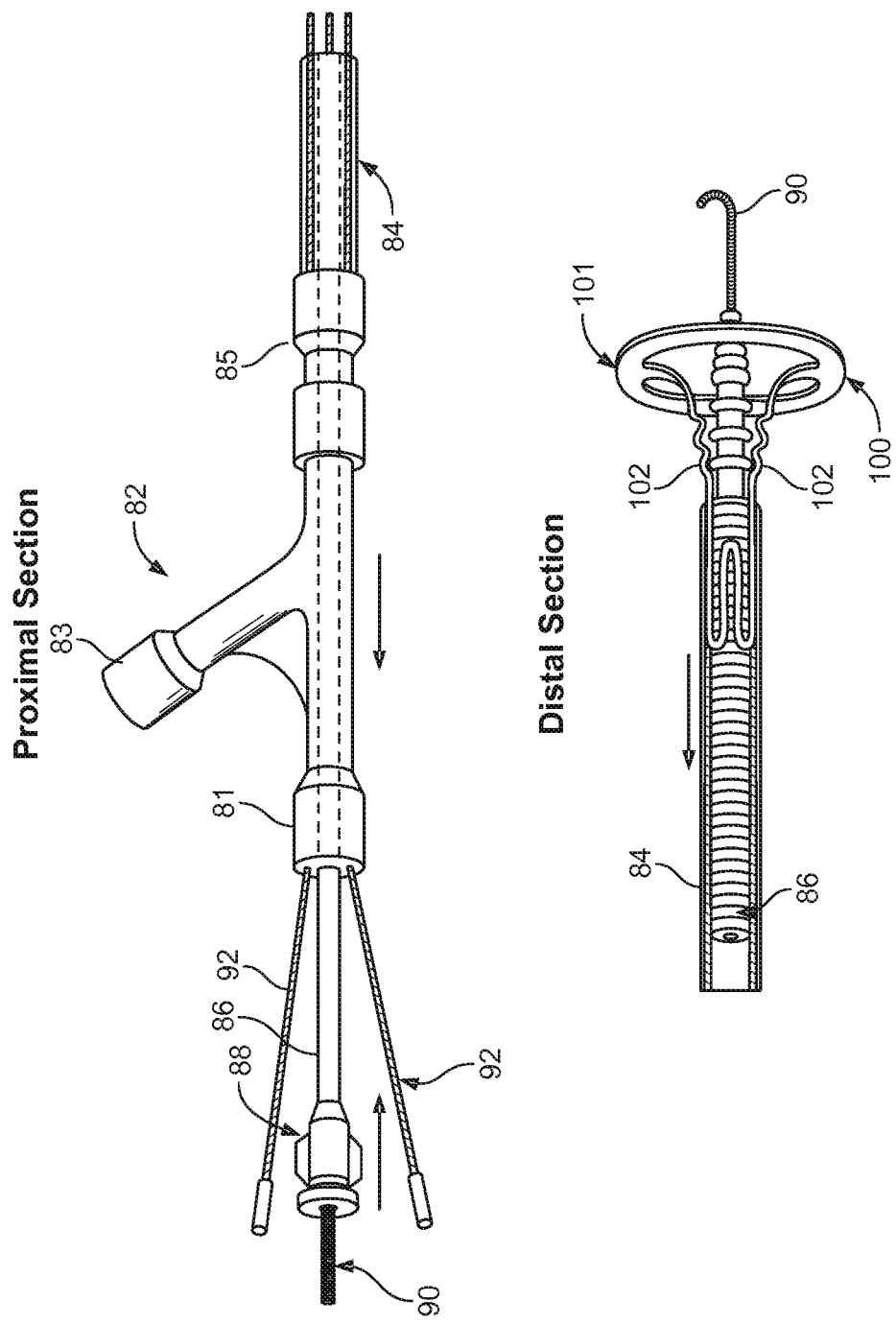
Figure 5D:
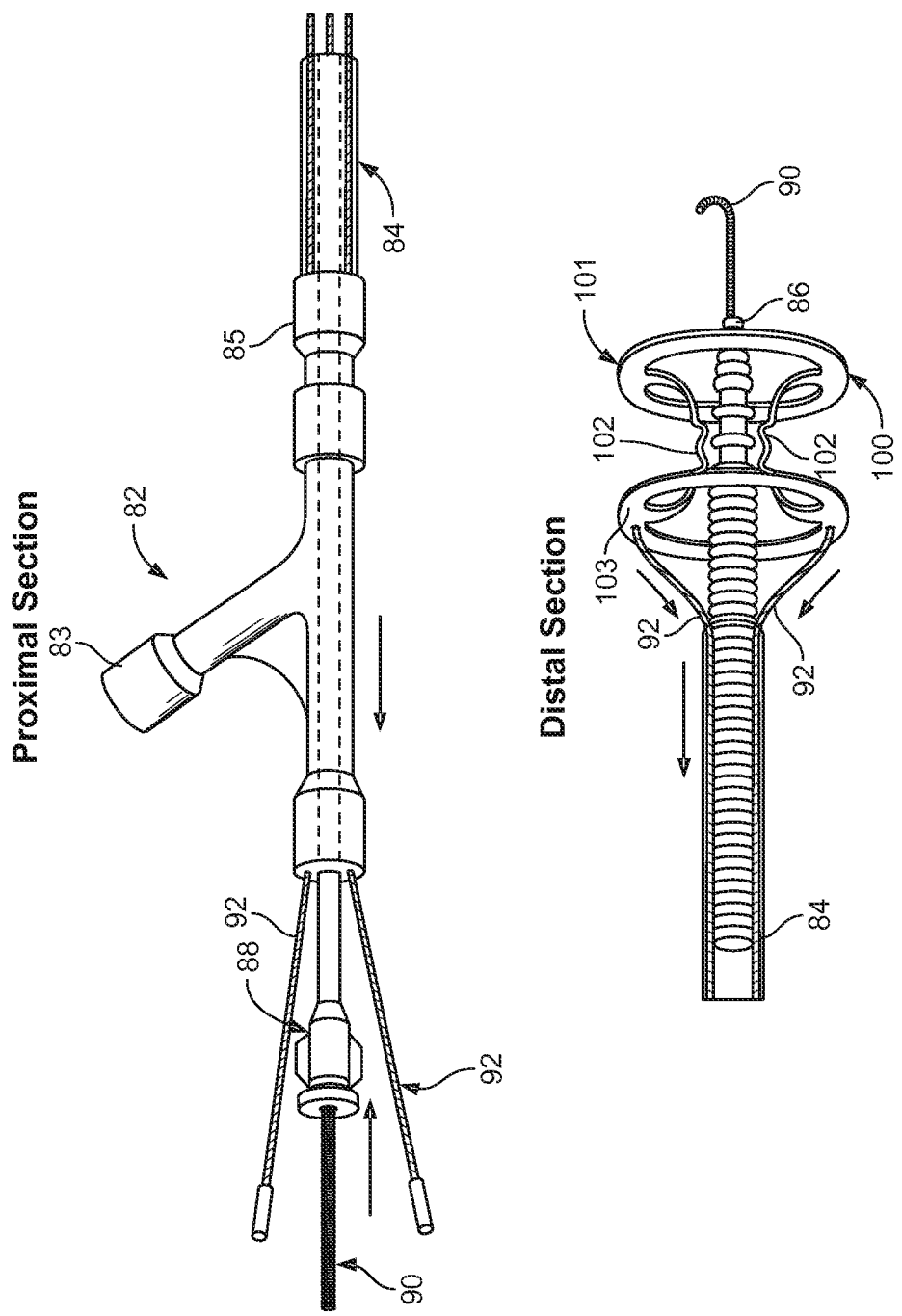

As shown in FIG. 5C, bridge members 102 of valve support 100 continue to be expanded by relative proximal movement of elongate body 84. This can be performed by proximal movement of the elongate body (as indicated by the arrow), by distally advancing lumen 86, or any combination of the two. Continued relative movement of elongate body 84 eventually causes second support element 103 to expand to a deployed configuration, as shown in FIG. 5D. As second support element 103 self-expands, coupling members 92 can extend radially outward along with support element 103.

Once the valve support is determined to be positioned in place, guiding lumen 92 can be removed to allow for a replacement heart valve to be positioned within the valve support, an example of which is shown in FIGS. 4A-4D.

Figure 6:
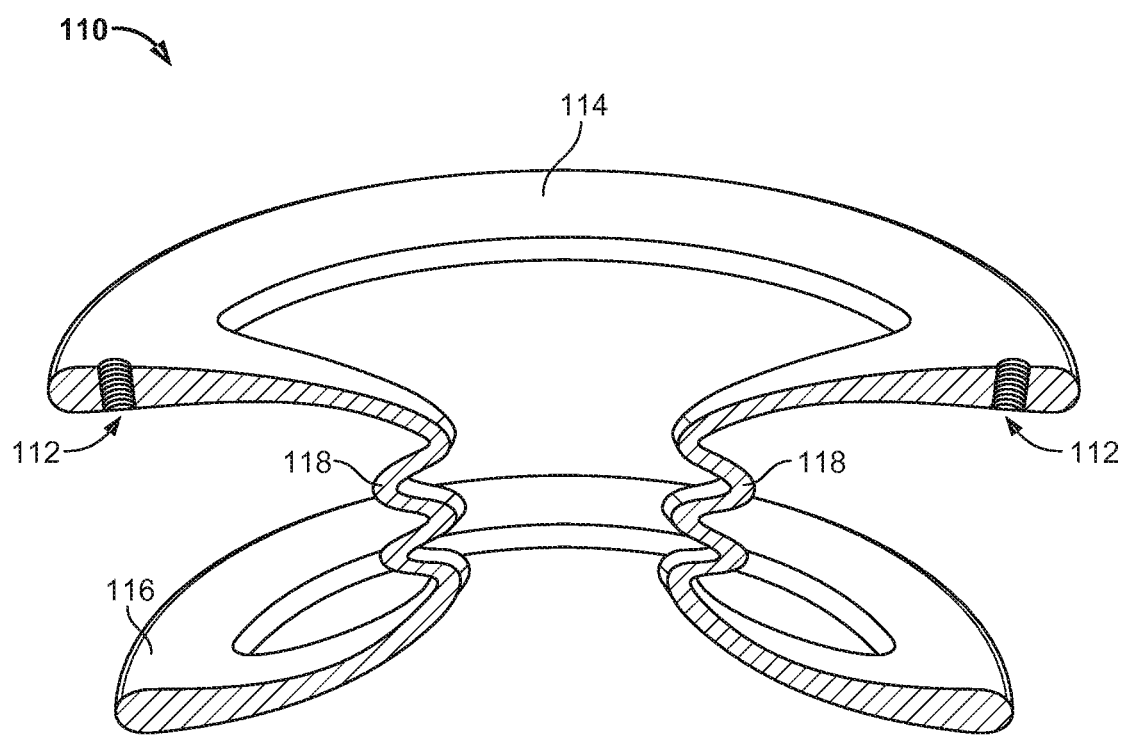
FIG. 6 illustrates a sectional view of an exemplary replacement mitral valve support.

FIG. 6 illustrates a section view of one-piece valve support 110, including first support element 114, second support element 116, bridging members 118, and coupling elements 112, which are shown as threaded bores and are adapted to securingly engage threaded portions of coupling members, examples of which are described above.

Figure 8A:
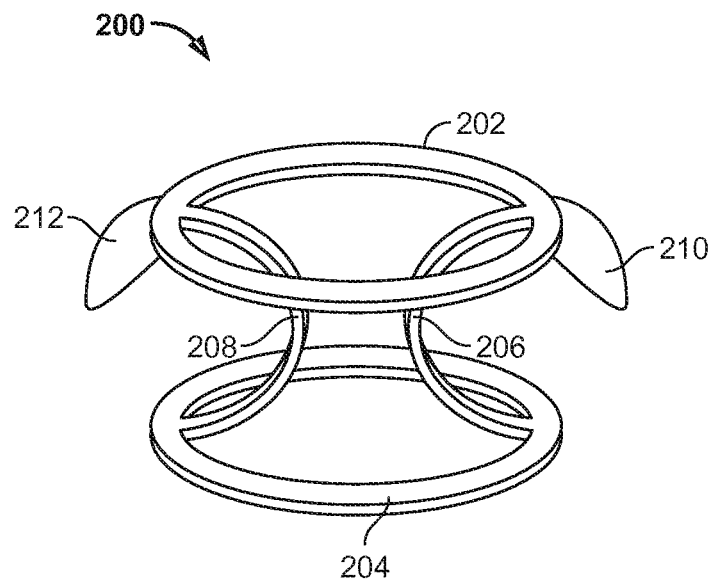
FIGS. 8A and 8B illustrate an embodiment comprising seals to reduce leakage.
Figure 8B:
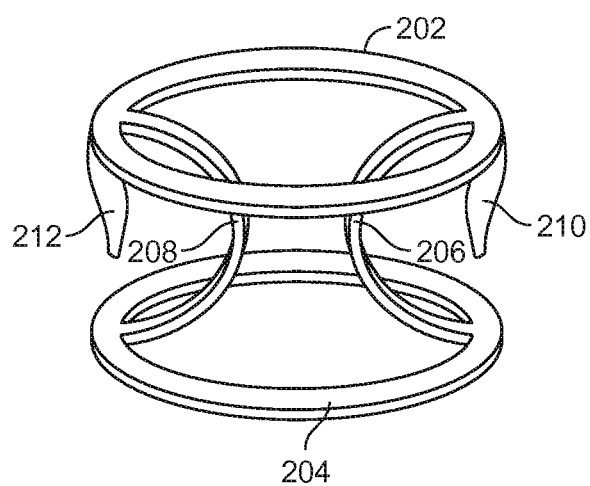

FIGS. 8A and 8B illustrate an alternative embodiment of a valve support. Valve support 200 includes components to mitigate para-valvular leakage. In addition to support elements 202 and 204 and bridge members 206 and 208, valve support 200 includes one or more flaps 210 and 212. The flaps extend coverage of the valve support system and help mitigate para-valvular leakage, functioning similarly to mudflaps on an automobile. During delivery exemplary flaps 210 and 212 are tucked around or against superior support element 202 as shown in FIG. 8B, and upon deployment from the catheter, flaps expand or extend to the configuration shown in FIG. 8A (native valve not shown for clarity). The flaps can be made of a flexible biocompatible material such as a wide variety of polymeric compositions. The flaps can be secured to the valve support by any suitable mechanism, such as by suturing the flaps to the support element, or to covered material, and using the bridge member to prevent the suture material from being displaced.

When deployed, in some embodiments the flaps are disposed above the annulus and over the side of the superior support element, which may not be extending all the way to the atrial wall. This can extend coverage of the valve support system for a few millimeters, reducing para-valvular leakage. Alternatively, in some embodiments in which the support element is larger, the flaps are urged against the atrial tissue. In this use, the flaps act as an additional seal when the valve support system is in place. The one or more flaps can therefore be a component of the valve support system that reduces para-valvular leakage and/or acts as an additional seal.

While some embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A two-step method of replacing a patient's mitral valve, comprising:
   endovascularly delivering a valve support to a location near a subject's mitral valve, the valve support comprising a first support element, a second support element, and first and second bridging members extending from the first and second support elements, wherein said valve support is configured to have a collapsed delivery configuration and an expanded deployed configuration;
   expanding the first support element from a collapsed first support delivery configuration to a deployed first support configuration secured against cardiac tissue below the plane of the mitral valve annulus;
   expanding the bridge members from collapsed bridge delivery configurations to expanded bridge deployed configurations positioned in general alignment with the coaptation points of the native mitral valve leaflets; and
   expanding the second support element from a collapsed second support delivery configuration to an expanded second support deployed configuration secured against left atrial tissue above the plane of the mitral valve annulus;
   wherein the native valve leaflets function after said expansion of said second support element;
   and subsequently delivering a replacement mitral valve and securing said replacement mitral valve to the valve support.

2. The method of claim 1, wherein expanding the first support element comprises allowing the first support element to self-expand against cardiac tissue.

3. The method of claim 1, wherein expanding each of the bridge members comprises allowing the bridge members to assume the expanded deployed bridge configuration in which the bridge members extend radially inward from the first and second support elements.

4. The method of claim 1, wherein expanding the second support element against left atrial tissue comprises allowing the second support element to self-expand.

5. The method of claim 1, wherein expanding the first support element comprises expanding the first support element to the expanded first support deployed configuration having a generally annular shape.

6. The method of claim 1, wherein expanding the first support element comprises expanding the first support element secured against papillary tendons.

7. The method of claim 6, wherein expanding the first support element comprises expanding the first support element secured against papillary tendons without displacing the papillary tendons.

8. The method of claim 1, wherein expanding the first support element occurs before expanding the second support element.

9. The method of claim 1, wherein expanding the bridge members comprises allowing the bridge members to symmetrically extend from the first support element to the second support element.

10. The method of claim 1, wherein expanding the bridge members comprises allowing the bridge members to extend from the first and second support elements about 180 degrees from one another.

11. The method of claim 1, wherein expanding the second support element comprises expanding the second support element to the expanded second support deployed configuration in which the second support element has a dimension larger than a dimension of the first support element in the expanded first support deployed configuration.

12. The method of claim 1, wherein securing the replacement mitral valve to the valve support comprises expanding the replacement mitral valve from a collapsed valve delivery configuration to an expanded valve deployed configuration.

13. The method of claim 12, wherein expanding the replacement mitral valve comprises expanding the replacement mitral valve with a balloon.

14. The method of claim 12, wherein expanding the replacement mitral valve comprises allowing the replacement mitral valve to self-expand.

15. The method of claim 1, wherein securing the replacement mitral valve to the valve support comprises securing the replacement mitral valve radially within the valve support.

16. The method of claim 1, wherein securing the replacement mitral valve to the valve support comprises locking a replacement mitral valve element with a valve support element to lock the replacement mitral valve to the valve support.

17. The method of claim 16, wherein the bridge members each comprise a bridge lock element and the replacement mitral valve comprises a plurality of lock elements, and the locking step comprises locking one of the plurality of lock elements with one of the bridge lock elements and locking a second of the plurality of lock elements with the other of the bridge lock elements.

* * * * *